United States Patent
Wilson et al.

(10) Patent No.: US 12,065,511 B2
(45) Date of Patent: Aug. 20, 2024

(54) AROMATIC-CATIONIC PEPTIDES AND USES OF SAME

(71) Applicant: STEALTH BIOTHERAPEUTICS INC., Needham, MA (US)

(72) Inventors: D. Travis Wilson, Newton, MA (US); Marc W. Andersen, Raleigh, NC (US); Elizabeth Mead, Hertfordshire (GB)

(73) Assignee: STEALTH BIOTHERAPEUTICS INC., Needham, MA (US)

( * ) Notice: Subject to any disclaimer, the term of this patent is extended or adjusted under 35 U.S.C. 154(b) by 0 days.

(21) Appl. No.: 16/818,560

(22) Filed: Mar. 13, 2020

(65) Prior Publication Data
US 2021/0040149 A1   Feb. 11, 2021

Related U.S. Application Data

(63) Continuation of application No. 15/865,434, filed on Jan. 9, 2018, now abandoned, which is a continuation of application No. 14/363,035, filed on Jun. 5, 2014, which is a continuation of application No. PCT/US2012/067984, filed on Dec. 5, 2012, now abandoned.

(60) Provisional application No. 61/569,120, filed on Dec. 9, 2011.

(51) Int. Cl.
| | |
|---|---|
| C07K 5/10 | (2006.01) |
| A61K 38/06 | (2006.01) |
| A61K 38/07 | (2006.01) |
| C07C 229/26 | (2006.01) |
| C07D 209/16 | (2006.01) |
| C07K 5/06 | (2006.01) |
| C07K 5/065 | (2006.01) |
| C07K 5/068 | (2006.01) |
| C07K 5/072 | (2006.01) |
| C07K 5/08 | (2006.01) |
| C07K 5/087 | (2006.01) |
| C07K 5/09 | (2006.01) |
| C07K 5/107 | (2006.01) |
| C07K 5/11 | (2006.01) |
| G01N 33/68 | (2006.01) |

(52) U.S. Cl.
CPC ............... *C07K 5/10* (2013.01); *A61K 38/06* (2013.01); *A61K 38/07* (2013.01); *C07C 229/26* (2013.01); *C07D 209/16* (2013.01); *C07K 5/06* (2013.01); *C07K 5/06078* (2013.01); *C07K 5/06086* (2013.01); *C07K 5/06095* (2013.01); *C07K 5/08* (2013.01); *C07K 5/0812* (2013.01); *C07K 5/0815* (2013.01); *C07K 5/0817* (2013.01); *C07K 5/1016* (2013.01); *C07K 5/1019* (2013.01); *G01N 33/68* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 5,674,534 A | 10/1997 | Zale et al. | |
| 5,716,644 A | 2/1998 | Zale et al. | |
| 6,468,798 B1 | 10/2002 | Debs et al. | |
| 8,697,657 B2 | 4/2014 | Wilson | |
| 9,345,738 B2 * | 5/2016 | Wilson | A61P 25/28 |
| 9,561,258 B2 | 2/2017 | Wilson | |
| 9,636,378 B2 * | 5/2017 | Wilson | A61P 43/00 |
| 9,687,519 B2 * | 6/2017 | Wilson | A61P 11/00 |
| 9,877,997 B2 * | 1/2018 | Wilson | A61K 45/06 |
| 9,884,085 B2 * | 2/2018 | Wilson | A61K 31/401 |
| 9,943,563 B2 * | 4/2018 | Wilson | A61P 17/00 |
| 9,988,422 B2 * | 6/2018 | Wilson | A61P 7/02 |
| 10,047,395 B2 * | 8/2018 | Wilson | C12Q 1/6883 |
| 10,188,693 B2 * | 1/2019 | Wilson | A61K 31/366 |
| 10,201,585 B2 * | 2/2019 | Wilson | A61K 31/404 |
| 10,279,008 B2 * | 5/2019 | Wilson | A61K 31/137 |
| 10,293,020 B2 | 5/2019 | Wilson | |
| 10,322,159 B2 * | 6/2019 | Wilson | A61K 45/06 |
| 10,525,098 B2 * | 1/2020 | Wilson | A61K 38/07 |
| 10,627,392 B2 * | 4/2020 | Wilson | G01N 33/5094 |
| 10,646,539 B2 * | 5/2020 | Wilson | A61K 31/4245 |
| 10,702,577 B2 * | 7/2020 | Wilson | A61P 7/02 |
| 10,744,178 B2 * | 8/2020 | Wilson | A61P 9/12 |
| 10,793,597 B2 * | 10/2020 | Wilson | A61P 5/14 |
| 10,835,573 B2 * | 11/2020 | Wilson | A61K 31/401 |
| 11,083,771 B2 * | 8/2021 | Wilson | A61P 9/00 |

(Continued)

FOREIGN PATENT DOCUMENTS

| | | |
|---|---|---|
| CN | 1780851 | 5/2006 |
| CN | 100536909 C | 9/2009 |

(Continued)

OTHER PUBLICATIONS

All acronyms (retrieved from http://www.allacronyms.com/COQO/Coenzyme_QO on Nov. 20, 2015, 3 pages).

(Continued)

*Primary Examiner* — Ronald T Niebauer
(74) *Attorney, Agent, or Firm* — FOLEY & LARDNER LLP

(57) ABSTRACT

The disclosure provides compositions and methods relating to aromatic-cationic peptides. The methods comprise administering to the subject an effective amount of an aromatic-cationic peptide to subjects in need thereof. For example, the peptides may be administered to subjects in need of a mitochondrial-targeted antioxidant.

6 Claims, No Drawings
Specification includes a Sequence Listing.

(56) References Cited

U.S. PATENT DOCUMENTS

| | | | |
|---|---|---|---|
| 11,083,772 B2* | 8/2021 | Wilson | A61K 38/07 |
| 11,141,456 B2* | 10/2021 | Wilson | C12Y 402/01002 |
| 2006/0166881 A1* | 7/2006 | Hotchkiss | A61K 49/0043 |
| | | | 514/18.9 |
| 2007/0027087 A1 | 2/2007 | Szeto et al. | |
| 2007/0275872 A1 | 11/2007 | Cooper et al. | |
| 2011/0245183 A1 | 10/2011 | Perricone | |

FOREIGN PATENT DOCUMENTS

| | | |
|---|---|---|
| CN | 101939019 A | 1/2011 |
| CN | 101951936 | 1/2011 |
| JP | 2015-507611 A | 3/2015 |
| WO | WO-96/40073 A2 | 12/1996 |
| WO | WO-99/15154 A1 | 4/1999 |
| WO | WO-00/38651 A1 | 7/2000 |
| WO | WO-2011/082324 A1 | 7/2011 |
| WO | WO-2011/091357 A1 | 7/2011 |
| WO | WO-2011/106717 A1 | 9/2011 |
| WO | WO-2011/126940 | 10/2011 |
| WO | WO-2011/139992 A1 | 11/2011 |

OTHER PUBLICATIONS

Amselem, et al., "A Large-Scale Method for the Preparation of Sterile and Nonpyrogenic Liposomal Formulations of Defined Size Distributions for Clinical Use." Liposome Technology, 1993, vol. I, 2nd ed., CRC Press, pp. 502-525.
Bachem (retrieved from http://www.bachem.com/service-support/faq/nomenclature/ on Nov. 20, 2015).
BLAST search (BLAST Search of RYKF retrieved from https://blast.ncbi.nim.nih.gov/Blast.cgi on Jun. 15, 2017, 7 pages.
Chonn et al., "Recent Advances in Liposomal Drug-Delivery Systems," Curr. Opin. Biotechnol., Dec. 1995, vol. 6, Issue 6, pp. 698-708.
CN First Office Action on 201710524414.8, dated Apr. 8, 2020 (with English translation) (14 pages).
Examination Report in AU Patent Application No. 2012347931 mailed Dec. 22, 2017 (5 pages).
Examination Report in EP Patent Application No. 15177562.4 mailed Feb. 15, 2018 (8 pages).
Extended European Search Report in EP Application No. 15177562.4 mailed Mar. 8, 2016 (9 pages).
Extended European Search Report in EP Patent Application No. 18190582.9 dated Mar. 11, 2019 (11 pages).
Extended European Search Report on EP Patent Application No. 19202295.2 dated Apr. 1, 2020 (11 pages).
Final Office Action in U.S. Appl. No. 14/363,035 mailed Aug. 10, 2016.
Final Rejection in JP Patent Application No. 2014-546031 mailed Jul. 3, 2017 (with English translation) (5 pages).
First Examination Report in AU Patent Application No. 2012347931 mailed Jan. 25, 2017 (4 pages).
First Examination Report in AU Patent Application No. 2017276158 dated Nov. 21, 2018 (2 pages).
First Office Action in CN Patent Application No. 201280066416.2 dated Jul. 23, 2015 (English translation) (15 pages).
Gregoriardis, "Engineering Liposomes for Drug Delivery: Progress and Problems," TIBTECH, Dec. 1995, vol. 13, pp. 527-537, 11 pages.
Guo, et al. "Structures and properties of antioxidative peptides derived from royal jelly protein." Food Chemistry, vol. 113 (2009), pp. 238-245.
International Preliminary Report on Patentability in International Patent Application No. PCT/US2012/067984 issued Jun. 10, 2014, 7 pages.
International Search Report and Written Opinion in International Patent Application No. PCT/US2012/067984 mailed Mar. 12, 2013, 9 pages.
Kelley, et al., "Development of Novel Peptides for Mitochondrial Drug Delivery: Amino Acids Featuring Delocalized Lipophilic Cations," Pharmaceutical Research, Aug. 11, 2011, vol. 28, Article No. 2808, pp. 2808-2819 (abstract only).
Li, Yunbo et al., "Detection of mitochondria-derived reactive oxygen species production by the chemilumigenic probes lucigenin and luminol," Biochim. Bioiphys. Acta., (Jun. 28, 1999), vol. 1428, Issue 1, pp. 1-12.
Lichtenberg et al. "Liposomes: Preparation, Characterization, and Preservation," Methods Biochem. Anal., 1998, vol. 33, pp. 337-462.
Lim, Kelvin H.H. et al., "The effects of ischaemic preconditioning, diazoxide and 5-hydroxydecanoate on rat heart mitochondrial volume and respiration," J Physiol, (2002), vol. 545, Issue 3, pp. 961-974.
Mizuguchi, et al., "Intratumor administration of fusogenic liposomes containing fragment A of diphtheria toxin suppresses tumor growth." Cancer Lett., Feb. 26, 1996, vol. 100, Issue 1, pp. 63-69.
Non-Final Office Action in U.S. Appl. No. 14/363,035 dated Dec. 3, 2015.
Non-Final Office Action in U.S. Appl. No. 14/363,035 mailed Jul. 12, 2017.
Non-Final Office Action in U.S. Appl. No. 15/865,434 dated Sep. 16, 2019.
Notification of Reexamination in CN Patent Application No. 201280066416.2 dated Apr. 19, 2018 (with English translation) (9 pages).
Office Action in CA Patent Application No. 2,858,550 dated Sep. 18, 2018 (4 pages).
Office Action in CA Patent Application No. 2858550 dated Aug. 12, 2019 (4 pages).
Office Action in JP Patent Application No. 2014-546031, mailed Oct. 12, 2016 (English translation) (7 pages).
Office Action in JP Patent Application No. 2017-212657 dated Oct. 29, 2018 (with English translation) (7 pages).
Office Action in JP Patent Application No. 2019-085146 dated Apr. 28, 2020 (with English translation) (6 pages).
Reddy, "Controlled-Release, Pegylation, Liposomal Formulations: New Mechanisms in the Delivery of Injectable Drugs," Ann Pharmacother., Jul./Aug. 2000, vol. 34, pp. 915-923.
Schiller, Peter W. et al., "Synthesis and In Vitro Opioid Activity Profiles of DALDA Analogues," European Journal of Medicinal Chemistry, (Oct. 2000), vol. 35, Issue 10, pp. 895-901.
Second Office Action in CN Patent Application No. 201280066416.2 dated Jun. 20, 2016 (with English translation) (16 pages).
Wang, et al., "Synthesis and Characterization of Biological Active Hydrazone Derivatives," Organic Chemistry, Dec. 31, 2007, vol. 27, No. 4, pp. 524-527.
Weiner, Alan L., "Liposomes for Protein Delivery: Selecting Manufacture and Development Processes," Immunomethods, Jun. 1994, vol. 4, No. 3, pp. 201-209.
Zhao, Guo-Min et al., "Comparision of [Dmt1]DALDA and DAMGO in Binding and G Protein Activation at $\mu$, $\delta$, and $\kappa$ Opioid Receptors," J Pharmacol Exp Ther., (2003), vol. 307, No. 3, pp. 947-954.
First Office Action and Search Report on CN Patent Application No. 201810783561.1 dated Jul. 5, 2021 (14 pages).

* cited by examiner

SEQUENCE LISTING

```
<160> NUMBER OF SEQ ID NOS: 27

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dmt

<400> SEQUENCE: 1

Arg Arg Xaa Phe
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dmt

<400> SEQUENCE: 2

Arg Xaa Lys Phe
1
```

```
<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dmt

<400> SEQUENCE: 3

Arg Xaa Lys Phe Cys
1               5

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dmt

<400> SEQUENCE: 4

Arg Xaa Phe Lys
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dmt

<400> SEQUENCE: 5

Arg Lys Xaa Phe
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dmt

<400> SEQUENCE: 6

Arg Lys Phe Xaa
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Dmt

<400> SEQUENCE: 7

Arg Phe Xaa Lys
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Tyr Lys Phe
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dmt

<400> SEQUENCE: 9

Xaa Phe Arg Lys
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dmt

<400> SEQUENCE: 10

Lys Phe Arg Xaa
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dmt

<400> SEQUENCE: 11

Phe Arg Xaa Lys
1
```

```
<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Arg Phe Lys
1

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Arg Phe Lys Glu Cys Gly
1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dmt

<400> SEQUENCE: 14

Phe Xaa Arg Lys
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dmt

<400> SEQUENCE: 15

Arg Xaa Lys Phe
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dmt

<400> SEQUENCE: 16

His Xaa Lys Phe
```

```
<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dmt

<400> SEQUENCE: 17

Lys Xaa Lys Phe
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Arg Phe Lys
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dmt

<400> SEQUENCE: 19

Arg Xaa Lys Phe
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dmt

<400> SEQUENCE: 20

Arg Xaa Lys Phe
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: Dmt

<400> SEQUENCE: 21

Phe Xaa Arg Lys
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dmt

<400> SEQUENCE: 22

Phe Lys Xaa Arg
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dmt

<400> SEQUENCE: 23

Xaa Arg Lys Phe
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dmt

<400> SEQUENCE: 24

Lys Xaa Arg Phe
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dmt

<400> SEQUENCE: 25

Phe Xaa Lys Arg
```

-continued

```
<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dmt

<400> SEQUENCE: 26

Arg Lys Xaa Phe
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dmt

<400> SEQUENCE: 27

Arg Xaa Phe Lys
1
```

AROMATIC-CATIONIC PEPTIDES AND USES OF SAME

CROSS-REFERENCE TO RELATED APPLICATIONS

This Application is a continuation of U.S. application Ser. No. 15/865,434, filed Jan. 9, 2018, which is a continuation of U.S. application Ser. No. 14/363,035, filed Jun. 5, 2014, which is the U.S. 371c National Stage Application of International Application No. PCT/US2012/067984, filed Dec. 5, 2012, which claims the benefit of and priority to U.S. Provisional Application No. 61/569,120 filed Dec. 9, 2011, which is incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 13, 2021, is named 091151-1303_SL.txt and is 6,662 bytes in size.

TECHNICAL FIELD

The present technology relates generally to compositions and methods of preventing or treating disease. In particular, the methods relate to the administration of aromatic-cationic peptides to a subject in need thereof.

BACKGROUND

The aromatic-cationic peptides disclosed herein are useful in therapeutic applications relating to oxidative damage and cell death. When administered to a mammal in need thereof, the peptides localize to the mitochondria and improve the integrity and function of the organelle. Administration of the peptides to a subject in need thereof reduces the number of mitochondria undergoing mitochondrial permeability transition, reduces the level of oxidative damage to cells and tissues, and increases the rate of mitochondrial ATP synthesis.

SUMMARY

In one aspect, the present invention provides an aromatic-cationic peptide or a pharmaceutically acceptable salt thereof. In some embodiments, the salt comprises trifluoroacetate salt or acetate salt. In some embodiments, the peptide is selected from the group consisting of:

6-Butyric acid CoQ0-Phe-D-Arg-Phe-Lys-NH$_2$
6-Decanoic acid CoQ0-Phe-D-Arg-Phe-Lys-NH$_2$
Arg-Arg-Dmt-Phe (SEQ ID NO: 1)
Arg-Cha-Lys
Arg-Dmt
Arg-Dmt-Arg
Arg-Dmt-Lys
Arg-Dmt-Lys-Phe (SEQ ID NO: 2)
Arg-Dmt-Lys-Phe-Cys (SEQ ID NO: 3)
Arg-Dmt-Phe
Arg-Dmt-Phe-Lys (SEQ ID NO: 4)
Arg-Lys-Dmt-Phe (SEQ ID NO: 5)
Arg-Lys-Phe-Dmt (SEQ ID NO: 6)
Arg-Phe-Dmt-Lys (SEQ ID NO: 7)
Arg-Phe-Lys
Arg-Trp-Lys
Arg-Tyr-Lys
Arg-Tyr-Lys-Phe (SEQ ID NO: 8)
D-Arg-D-Dmt-D-Lys-D-Phe-NH$_2$
D-Arg-D-Dmt-D-Lys-L-Phe-NH$_2$
D-Arg-D-Dmt-L-Lys-D-Phe-NH$_2$
D-Arg-D-Dmt-L-Lys-L-Phe-NH$_2$
D-Arg-Dmt-D-Lys- NH$_2$
D-Arg-Dmt-D-Lys-Phe-NH$_2$
D-Arg-Dmt-Lys-D-Phe-NH$_2$
D-Arg-Dmt-Lys-NH$_2$
D-Arg-Dmt-Lys-Phe-Cys
D-Arg-Dmt-NH$_2$
D-Arg-L-Dmt-D-Lys-D-Phe-NH$_2$
D-Arg-L-Dmt-D-Lys-L-Phe-NH$_2$
D-Arg-L-Dmt-L-Lys-D-Phe-NH$_2$
D-Arg-Phe-Lys-NH$_2$
D-Arg-Trp-Lys-NH$_2$
D-Arg-Tyr-Lys-NH$_2$
Dmt-Arg
Dmt-Lys
Dmt-Lys-D-Phe-NH$_2$
Dmt-Lys-NH$_2$
Dmt-Lys-Phe
Dmt-Lys-Phe
Dmt-Lys-Phe-NH$_2$
Dmt-Phe-Arg-Lys (SEQ ID NO: 9)
H-Arg-D-Dmt-Arg-NH$_2$
H-Arg-D-Dmt-Lys-NH$_2$
H-Arg-D-Dmt-Lys-Phe-NH$_2$
H-Arg-D-Dmt-NH$_2$
H-Arg-Dmt-Lys-Phe-NH$_2$ (SEQ ID NO: 15)
H-D-Arg-2,6-dichloro-L-tyrosine-L-Lys-L-Phe-NH$_2$
H-D-Arg-2,6-dichlorotyrosine-Lys-Phe-NH$_2$
H-D-Arg-2,6-difluoro-L-tyrosine-L-Lys-L-Phe-NH$_2$
H-D-Arg-2,6-difluorotyrosine-Lys-Phe-NH$_2$
H-D-Arg-2,6-dimethyl-L-phenylalanine-L-Lys-L-Phe-NH$_2$
H-D-Arg-2,6-dimethylphenylalanine-Lys-Phe-NH$_2$
H-D-Arg-4-methoxy-2,6-dimethyl-L-tyrosine-L-Lys-L-Phe-NH$_2$
H-D-Arg-4-methoxy-2,6-dimethyltyrosine-Lys-Phe-NH$_2$
H-D-Arg-Arg-Dmt-Phe-NH$_2$
H-D-Arg-Cha-Lys-NH$_2$
H-D-Arg-D-Dmt-D-Lys-D-Phe-NH$_2$
H-D-Arg-D-Dmt-Lys-Phe-NH$_2$
H-D-Arg-D-Dmt-NH$_2$
H-D-Arg-Dmt-D-Lys-D-Phe-NH$_2$
H-D-Arg-Dmt-Lys-2,6-dimethylphenylalanine-NH$_2$
H-D-Arg-Dmt-Lys-3-hydroxyphenylalanine-NH$_2$
H-D-Arg-Dmt-Lys-NH$_2$
H-D-Arg-Dmt-Lys-OH
H-D-Arg-Dmt-Lys-Phe-OH
H-D-Arg-Dmt-N6-acetyllysine-Phe-NH$_2$
H-D-Arg-Dmt-OH
H-D-Arg-Dmt-Phe-Lys-NH$_2$
H-D-Arg-Dmt-Phe-NH$_2$
H-D-Arg-D-Phe-L-Lys-L-Phe-NH$_2$
H-D-Arg-D-Trp-L-Lys-L-Phe-NH$_2$
H-D-Arg-D-Tyr-L-Lys-L-Phe-NH$_2$
H-D-Arg-L-Dmt-L-Lys-2,6-dimethyl-L-phenylalanine-NH$_2$
H-D-Arg-L-Dmt-L-Lys-3-hydroxy-L-phenylalanine-NH$_2$
H-D-Arg-L-Dmt-L-Lys-D-Dmt-NH$_2$
H-D-Arg-L-Dmt-L-Lys-D-Trp-NH$_2$
H-D-Arg-L-Dmt-L-Lys-D-Tyr-NH$_2$
H-D-Arg-L-Dmt-L-Lys-L-Dmt-NH$_2$
H-D-Arg-L-Dmt-L-Lys-L-Dmt-NH$_2$
H-D-Arg-L-Dmt-L-Lys-L-Trp-NH$_2$
H-D-Arg-L-Dmt-L-Lys-L-Tyr-NH$_2$
H-D-Arg-L-Dmt-L-Phe-L-Lys-NH$_2$
H-D-Arg-L-Dmt-N6-acetyl-L-lysine-L-Phe-NH$_2$
H-D-Arg-L-Lys-L-Dmt-L-Phe-NH$_2$
H-D-Arg-L-Lys-L-Phe-L-Dmt-NH$_2$
H-D-Arg-L-Phe-L-Dmt-L-Lys-NH$_2$
H-D-Arg-L-Phe-L-Lys-L-Dmt-NH$_2$
H-D-Arg-L-Phe-L-Lys-L-Phe-NH$_2$
H-D-Arg-L-Trp-L-Lys-L-Phe-NH$_2$
H-D-Arg-L-Tyr-L-Lys-L-Phe-NH$_2$
H-D-Arg-Lys-Dmt-Phe-NH$_2$
H-D-Arg-Lys-Phe-Dmt-NH$_2$
H-D-Arg-Phe-Dmt-Lys-NH$_2$
H-D-Arg-Phe-Lys-Dmt-NH$_2$
H-D-Arg-Tyr-Lys-Phe-NH$_2$
H-D-Dmt-Arg-NH$_2$ H-D-His-L-Dmt-L-Lys-L-Phe-NH$_2$
H-D-Lys-L-Dmt-L-Lys-L-Phe-NH$_2$
H-Dmt-D-Arg-Lys-Phe-NH$_2$
H-Dmt-D-Arg-NH$_2$
H-Dmt-D-Arg-Phe-Lys-NH$_2$
H-Dmt-D-Phe-Arg-Lys-NH$_2$
H-Dmt-Lys-D-Arg-Phe-NH$_2$
H-Dmt-Lys-Phe-D-Arg-NH$_2$
H-Dmt-Phe-D-Arg-Lys-NH$_2$
H-Dmt-Phe-Lys-D-Arg-NH$_2$
H-D-N2-acetylarginine-Dmt-Lys-Phe-NH$_2$
H-D-N8-acetylarginine-Dmt-Lys-Phe-NH$_2$
H-D-Phe-D-Arg-D-Phe-D-Lys-NH$_2$
H-L-Dmt-D-Arg-L-Lys-L-Phe-NH$_2$
H-L-Dmt-D-Arg-L-Phe-L-Lys-NH$_2$
H-L-Dmt-L-Lys-D-Arg-L-Phe-NH$_2$
H-L-Dmt-L-Lys-L-Phe-D-Arg-NH$_2$
H-L-Dmt-L-Phe-D-Arg-L-Lys-NH$_2$
H-L-Dmt-L-Phe-L-Lys-D-Arg-NH$_2$
H-L-His-L-Dmt-L-Lys-L-Phe-NH$_2$ (SEQ ID NO: 16)
H-L-Lys-D-Arg-L-Dmt-L-Phe-NH$_2$
H-L-Lys-D-Arg-L-Phe-L-Dmt-NH$_2$
H-L-Lys-L-Dmt-D-Arg-L-Phe-NH$_2$
H-L-Lys-L-Dmt-L-Lys-L-Phe-NH$_2$ (SEQ ID NO: 17)
H-L-Lys-L-Dmt-L-Phe-D-Arg-NH$_2$
H-L-Lys-L-Phe-D-Arg-L-Dmt-NH$_2$
H-L-Lys-L-Phe-L-Dmt-D-Arg-NH$_2$
H-L-Phe-D-Arg-L-Dmt-L-Lys-NH$_2$
H-L-Phe-D-Arg-L-Lys-L-Dmt-NH$_2$
H-L-Phe-L-Dmt-D-Arg-L-Lys-NH$_2$
H-L-Phe-L-Dmt-L-Lys-D-Arg-NH$_2$
H-L-Phe-L-Lys-D-Arg-L-Dmt-NH$_2$
H-L-Phe-L-Lys-L-Dmt-D-Arg-NH$_2$
H-Lys-D-Arg-Dmt-Phe-NH$_2$
H-Lys-D-Arg-Phe-Dmt-NH$_2$
H-Lys-Dmt-D-Arg-Phe-NH$_2$
H-Lys-Dmt-Phe-D-Arg-NH$_2$
H-Lys-D-Phe-Arg-Dmt-NH$_2$
H-Lys-Phe-D-Arg-Dmt-NH$_2$
H-Lys-Phe-Dmt-D-Arg-NH$_2$
H-N2-acetyl-D-arginine-L-Dmt-L-Lys-L-Phe-NH$_2$
H-N7-acetyl-D-arginine-Dmt-Lys-Phe-NH$_2$
H-Phe(d5)-D-Arg-Phe(d5)-Lys-NH$_2$
H-Phe-Arg-Phe-Lys-NH$_2$ (SEQ ID NO: 18)
H-Phe-D-Arg-Dmt-Lys-NH$_2$
H-Phe-D-Arg-Dmt-Lys-NH$_2$
H-Phe-D-Arg-D-Phe-Lys-NH$_2$
H-Phe-D-Arg-Lys-Dmt-NH$_2$
H-Phe-D-Arg-Phe-D-Lys-NH$_2$
H-Phe-D-Arg-Phe-Lys-Glu-Cys-Gly-NH$_2$
H-Phe-Dmt-Arg-Lys-NH$_2$
H-Phe-Dmt-D-Arg-Lys-NH$_2$
H-Phe-Dmt-Lys-D-Arg-NH$_2$
H-Phe-Lys-D-Arg-Dmt-NH$_2$
H-Phe-Lys-Dmt-D-Arg-NH$_2$
L-Arg-D-Dmt-D-Lys-D-Phe-NH$_2$
L-Arg-D-Dmt-D-Lys-D-Phe-NH$_2$
L-Arg-D-Dmt-D-Lys-L-Phe-NH$_2$
L-Arg-D-Dmt-D-Lys-L-Phe-NH$_2$
L-Arg-D-Dmt-L-Lys-D-Phe-NH$_2$
L-Arg-D-Dmt-L-Lys-D-Phe-NH$_2$
L-Arg-D-Dmt-L-Lys-L-Phe-NH$_2$
L-Arg-D-Dmt-L-Lys-L-Phe-NH$_2$
L-Arg-L-Dmt-D-Lys-D-Phe-NH$_2$
L-Arg-L-Dmt-D-Lys-D-Phe-NH$_2$
L-Arg-L-Dmt-D-Lys-L-Phe-NH$_2$
L-Arg-L-Dmt-D-Lys-L-Phe-NH$_2$
L-Arg-L-Dmt-L-Lys-D-Phe-NH$_2$
L-Arg-L-Dmt-L-Lys-D-Phe-NH$_2$
L-Arg-L-Dmt-L-Lys-L-Phe-NH$_2$ (SEQ ID NO: 19)
L-Arg-L-Dmt-L-Lys-L-Phe-NH$_2$ (SEQ ID NO: 19)
Lys-Dmt-Arf
Lys-Dmt-D-Arg-NH$_2$
Lys-Phe
Lys-Phe-Arg-Dmt (SEQ ID NO: 10)
Lys-Phe-NH$_2$
Lys-Trp-Arg
Lys-Trp-D-Arg-NH$_2$
Phe-Arg-Dmt-Lys (SEQ ID NO: 11)
Phe-Arg-Phe-Lys (SEQ ID NO: 12)
Phe-Arg-Phe-Lys (SEQ ID NO: 12)
Phe-Arg-Phe-Lys (SEQ ID NO: 12)
Phe-Arg-Phe-Lys (SEQ ID NO: 12)
Phe-Arg-Phe-Lys (SEQ ID NO: 12)
Phe-Arg-Phe-Lys-Glu-Cys-Gly (SEQ ID NO: 13)
Phe-Dmt-Arg-Lys (SEQ ID NO: 14)
Phe-Lys-Dmt
Phe-Lys-Dmt-NH$_2$
Succinic monoester CoQ0-Phe-D-Arg-Phe-Lys-NH$_2$ wherein Cha is cyclohexylalanine.

In one embodiment, the peptide is defined by formula I:

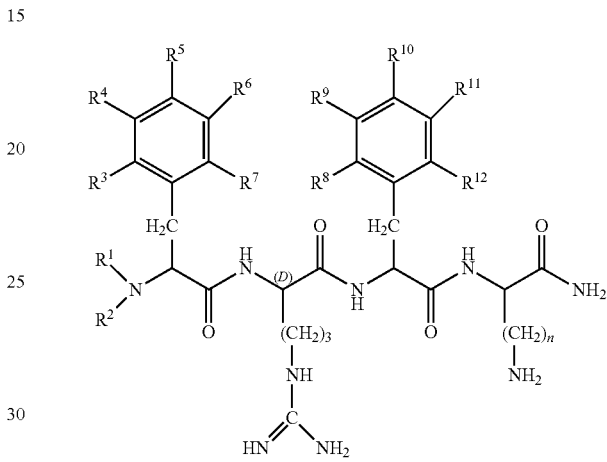

wherein $R^1$ and $R^2$ are each independently selected from
(i) hydrogen;
(ii) linear or branched $C_1$-$C_6$ alkyl;
(iii)

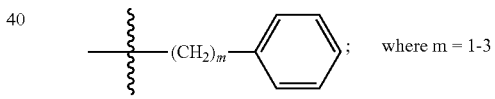; where m = 1-3

(iv)

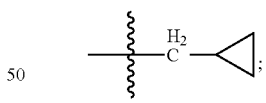;

(v)

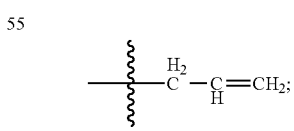;

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;

(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, $R^1$, $R^2$, $R^3$, $R^4$, $R^5$, $R^6$, $R^7$, $R^8$, $R'$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

In one embodiment, the peptide is defined by formula II:

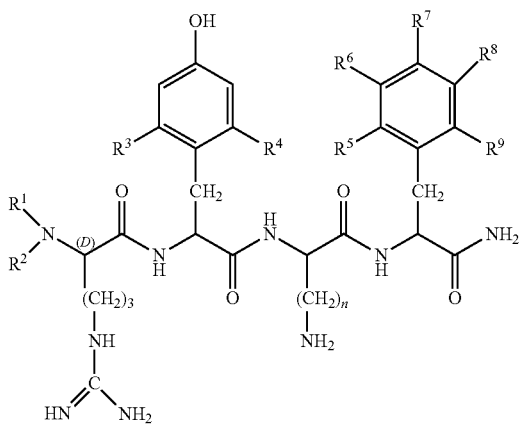

wherein $R^1$ and $R^2$ are each independently selected from
(i) hydrogen;
(ii) linear or branched $C_1$-$C_6$ alkyl;
(iii)

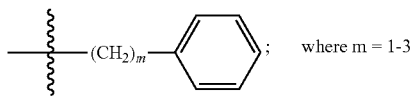; where m = 1-3

(iv)

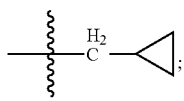;

(v)

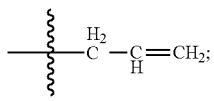;

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo;
$R^5$, $R^6$, $R^7$, $R^8$, and $R'$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In one embodiment, the aromatic-cationic peptides have a core structural motif of alternating aromatic and cationic amino acids. For example, the peptide may be a tetrapeptide defined by any of formulas III to VI set forth below:

| | |
|---|---|
| Aromatic-Cationic-Aromatic-Cationic | (Formula III) |
| Cationic-Aromatic-Cationic-Aromatic | (Formula IV) |
| Aromatic-Aromatic-Cationic-Cationic | (Formula V) |
| Cationic-Cationic-Aromatic-Aromatic | (Formula VI) | wherein, Aromatic is a residue selected from the group consisting of: Phe (F), Tyr (Y), Trp (W), and Cyclohexyl-alanine (Cha); and Cationic is a residue selected from the group consisting of: Arg (R), Lys (K), Norleucine (Nle), and 2-amino-heptanoic acid (Ahe).

In some embodiments, the peptide is defined by formula VII:

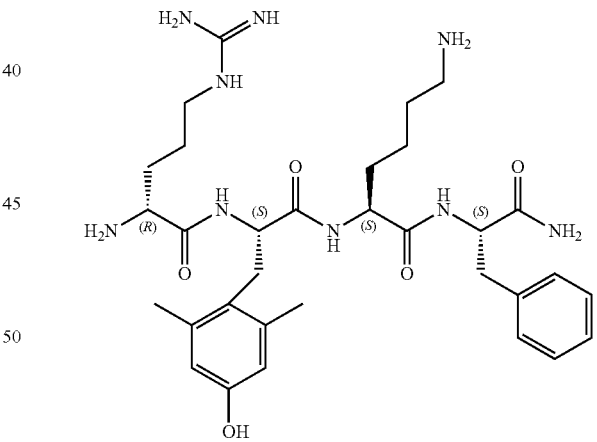

In some embodiments, the peptide is an isomer of formula VII, wherein the chiral centers of formula III are defined as H-(R)-Arg-(S)-DMT-(S)-Lys-(S)-Phe-NH2 (SEQ ID NO: 20), and wherein stereoisomers are described by the formulas

R—S—S—S

S—R—R—R

S—S—S—S

R—R—R—R

R—R—S—S

S—S—R—R

S—R—S—S

R—S—R—R

R—S—R—S

S—R—S—R

R—R—S—R

S—S—R—S

R—R—R—S

S—S—S—R

R—S—S—R

S—R—R—S

In some embodiments, the peptide is a constitutional isomer of formula VII selected from the group consisting of:

Arg-Dmt-Lys-Phe-NH$_2$ (SEQ ID NO: 19)
Phe-Dmt-Arg-Lys-NH$_2$ (SEQ ID NO: 21)
Phe-Lys-Dmt-Arg-NH$_2$ (SEQ ID NO: 22)
Dmt-Arg-Lys-Phe-NH$_2$ (SEQ ID NO: 23)
Lys-Dmt-Arg-Phe-NH$_2$ (SEQ ID NO: 24)
Phe-Dmt-Lys-Arg-NH$_2$ (SEQ ID NO: 25)
Arg-Lys-Dmt-Phe-NH$_2$ (SEQ ID NO: 26)
Arg-Dmt-Phe-Lys-NH$_2$ (SEQ ID NO: 27)

In some embodiments, the peptide is defined by formula VIII:

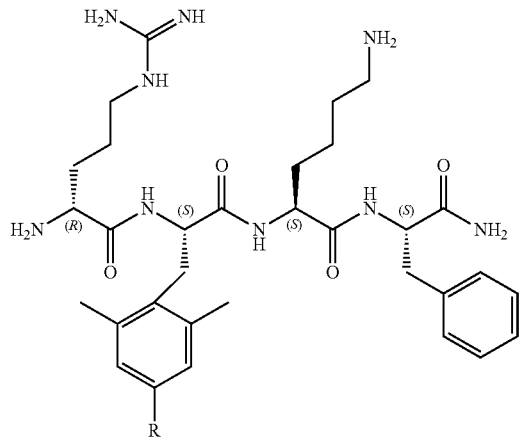

wherein R is selected from
(i) OMe, and
(ii) H.

In some embodiments, the peptide is defined by formula IX:

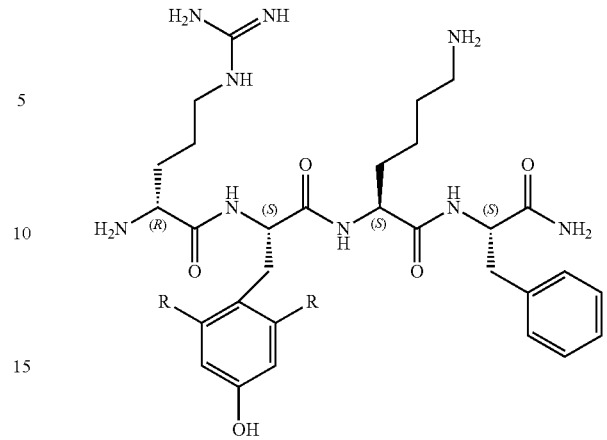

wherein R is selected from
(i) F,
(ii) Cl, and
(iii) H.

In some embodiments, the peptide is defined by formula X:

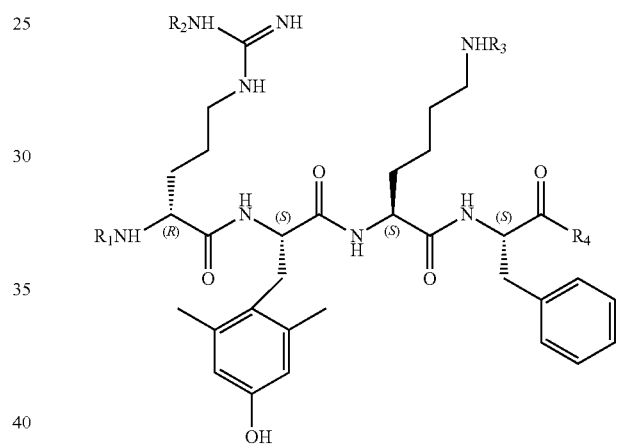

wherein $R^1$-$R^4$ are selected from
(i) Ac, (ii) H, (iii) H, (iv) H,
(i) H, (ii) Ac, (iii) H, (iv) H,
(i) H, (ii) H, (iii) Ac, (iv) H, and
(i) H, (ii) H, (iii) H, (iv) OH.

In one embodiment, the peptide is defined by formula XI:

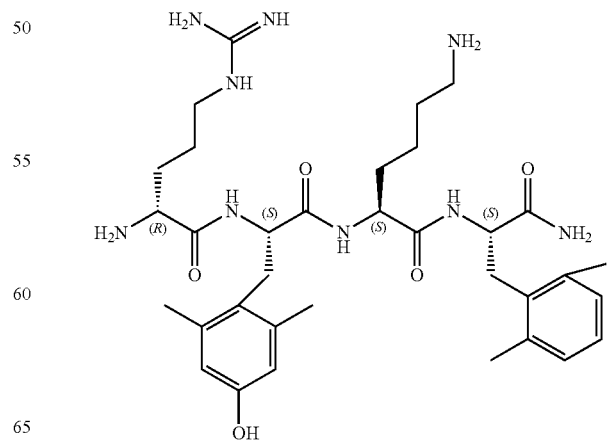

In some aspects, pharmaceutical compositions are provided herein. In some embodiments, the pharmaceutical compositions include one or more aromatic-cationic peptides or a pharmaceutically acceptable salt thereof, such as acetate salt or trifluoroacetate salt. In some embodiments, the pharmaceutical composition includes one or more pharmaceutically acceptable carriers.

In one aspect, the disclosure provides a method of reducing the number of mitochondria undergoing mitochondrial permeability transition (MPT), or preventing mitochondrial permeability transitioning in a mammal in need thereof, the method comprising administering to the mammal an effective amount of one or more aromatic-cationic peptides described herein, or a pharmaceutically salt thereof such as acteate salt or trifluoroacetate salt. In another aspect, the disclosure provides a method for increasing the ATP synthesis rate in a mammal in need thereof, the method comprising administering to the mammal an effective amount of one or more aromatic-cationic peptides described herein or a pharmaceutically salt thereof such as acetate salt or trifluoroacetate salt. In yet another aspect, the disclosure provides a method for reducing oxidative damage in a mammal in need thereof, the method comprising administering to the mammal an effective amount of one or more aromatic-cationic peptides described herein or a pharmaceutically salt thereof such as acteate salt or trifluoroacetate salt.

In some aspects, a method for determining the presence or amount of an aromatic-cationic peptide present in a subject is provided. Typically, the methods include detecting the peptide in a biological sample from the subject. In some embodiments, the peptide is detected during administration of the peptide to a subject; in some embodiments, the peptide is detected after administration of the peptide to a subject. In some embodiments, detecting includes HPLC, for example, reverse phase HPLC or ion exchange HPLC. In some embodiments, detection includes mass spectrometry.

In some embodiments, the biological sample comprises a fluid; in some embodiments, the biological sample comprises a cell. In some embodiments, the biological sample comprises a tissue. In other embodiments, the biological sample comprises a biopsy.

In some embodiments, the aromatic-cationic peptide that is detected is selected from the group consisting one or more of:

D-Arg-Dmt-Lys-Phe-$NH_2$
Dmt-D-Arg-Phe-Lys-$NH_2$
Phe-D-Arg-Dmt-Lys-$NH_2$
6-Butyric acid CoQ0-Phe-D-Arg-Phe-Lys-$NH_2$
6-Decanoic acid CoQ0-Phe-D-Arg-Phe-Lys-$NH_2$
Arg-Arg-Dmt-Phe (SEQ ID NO: 1)
Arg-Cha-Lys
Arg-Dmt
Arg-Dmt-Arg
Arg-Dmt-Lys
Arg-Dmt-Lys-Phe (SEQ ID NO: 2)
Arg-Dmt-Lys-Phe-Cys (SEQ ID NO: 3)
Arg-Dmt-Phe
Arg-Dmt-Phe-Lys (SEQ ID NO: 4)
Arg-Lys-Dmt-Phe (SEQ ID NO: 5)
Arg-Lys-Phe-Dmt (SEQ ID NO: 6)
Arg-Phe-Dmt-Lys (SEQ ID NO: 7)
Arg-Phe-Lys
Arg-Trp-Lys
Arg-Tyr-Lys
Arg-Tyr-Lys-Phe (SEQ ID NO: 8)
D-Arg-D-Dmt-D-Lys-D-Phe-$NH_2$
D-Arg-D-Dmt-D-Lys-L-Phe-$NH_2$
D-Arg-D-Dmt-L-Lys-D-Phe-$NH_2$
D-Arg-D-Dmt-L-Lys-L-Phe-$NH_2$ -continued D-Arg-Dmt-D-Lys- $NH_2$
D-Arg-Dmt-D-Lys-Phe-$NH_2$
D-Arg-Dmt-Lys-D-Phe-$NH_2$
D-Arg-Dmt-Lys-$NH_2$
D-Arg-Dmt-Lys-Phe-Cys
D-Arg-Dmt-$NH_2$
D-Arg-L-Dmt-D-Lys-D-Phe-$NH_2$
D-Arg-L-Dmt-D-Lys-L-Phe-$NH_2$
D-Arg-L-Dmt-L-Lys-D-Phe-$NH_2$
D-Arg-Phe-Lys-$NH_2$
D-Arg-Trp-Lys-$NH_2$
D-Arg-Tyr-Lys-$NH_2$
Dmt-Arg
Dmt-Lys
Dmt-Lys-D-Phe-$NH_2$
Dmt-Lys-$NH_2$
Dmt-Lys-Phe
Dmt-Lys-Phe
Dmt-Lys-Phe-$NH_2$
Dmt-Phe-Arg-Lys (SEQ ID NO: 9)
H-Arg-D-Dmt-Arg-$NH_2$
H-Arg-D-Dmt-Lys-$NH_2$
H-Arg-D-Dmt-Lys-Phe-$NH_2$
H-Arg-D-Dmt-$NH_2$
H-Arg-Dmt-Lys-Phe-$NH_2$ (SEQ ID NO: 15)
H-D-Arg-2,6-dichloro-L-tyrosine-L-Lys-L-Phe-$NH_2$
H-D-Arg-2,6-dichlorotyrosine-Lys-Phe-$NH_2$
H-D-Arg-2,6-difluoro-L-tyrosine-L-Lys-L-Phe-$NH_2$
H-D-Arg-2,6-difluorotyrosine-Lys-Phe-$NH_2$
H-D-Arg-2,6-dimethyl-L-phenylalanine-L-Lys-L-Phe-$NH_2$
H-D-Arg-2,6-dimethylphenylalanine-Lys-Phe-$NH_2$
H-D-Arg-4-methoxy-2,6-dimethyl-L-tyrosine-L-Lys-L-Phe-$NH_2$
H-D-Arg-4-methoxy-2,6-dimethyltyrosine-Lys-Phe-$NH_2$
H-D-Arg-Arg-Dmt-Phe-$NH_2$
H-D-Arg-Cha-Lys-$NH_2$
H-D-Arg-D-Dmt-D-Lys-D-Phe-$NH_2$
H-D-Arg-D-Dmt-Lys-Phe-$NH_2$
H-D-Arg-D-Dmt-$NH_2$
H-D-Arg-Dmt-D-Lys-D-Phe-$NH_2$
H-D-Arg-Dmt-Lys-2,6-dimethylphenylalanine-$NH_2$
H-D-Arg-Dmt-Lys-3-hydroxyphenylalanine-$NH_2$
H-D-Arg-Dmt-Lys-$NH_2$
H-D-Arg-Dmt-Lys-OH
H-D-Arg-Dmt-Lys-Phe-OH
H-D-Arg-Dmt-N6-acetyllysine-Phe-$NH_2$
H-D-Arg-Dmt-OH
H-D-Arg-Dmt-Phe-Lys-$NH_2$
H-D-Arg-Dmt-Phe-$NH_2$
H-D-Arg-D-Phe-L-Lys-L-Phe-$NH_2$
H-D-Arg-D-Trp-L-Lys-L-Phe-$NH_2$
H-D-Arg-D-Tyr-L-Lys-L-Phe-$NH_2$
H-D-Arg-L-Dmt-L-Lys-2,6-dimethyl-L-phenylalanine-$NH_2$
H-D-Arg-L-Dmt-L-Lys-3-hydroxy-L-phenylalanine-$NH_2$
H-D-Arg-L-Dmt-L-Lys-D-Dmt-$NH_2$
H-D-Arg-L-Dmt-L-Lys-D-Trp-$NH_2$
H-D-Arg-L-Dmt-L-Lys-D-Tyr-$NH_2$
H-D-Arg-L-Dmt-L-Lys-L-Dmt-$NH_2$
H-D-Arg-L-Dmt-L-Lys-L-Dmt-$NH_2$
H-D-Arg-L-Dmt-L-Lys-L-Trp-$NH_2$
H-D-Arg-L-Dmt-L-Lys-L-Tyr-$NH_2$
H-D-Arg-L-Dmt-L-Phe-L-Lys-$NH_2$
H-D-Arg-L-Dmt-N6-acetyl-L-lysine-L-Phe-$NH_2$
H-D-Arg-L-Lys-L-Dmt-L-Phe-$NH_2$
H-D-Arg-L-Lys-L-Phe-L-Dmt-$NH_2$
H-D-Arg-L-Phe-L-Dmt-L-Lys-$NH_2$
H-D-Arg-L-Phe-L-Lys-L-Dmt-$NH_2$
H-D-Arg-L-Phe-L-Lys-L-Phe-$NH_2$
H-D-Arg-L-Trp-L-Lys-L-Phe-$NH_2$
H-D-Arg-L-Tyr-L-Lys-L-Phe-$NH_2$
H-D-Arg-Lys-Dmt-Phe-$NH_2$
H-D-Arg-Lys-Phe-Dmt-$NH_2$
H-D-Arg-Phe-Dmt-Lys-$NH_2$
H-D-Arg-Phe-Lys-Dmt-$NH_2$
H-D-Arg-Tyr-Lys-Phe-$NH_2$
H-D-Dmt-Arg-$NH_2$
H-D-His-L-Dmt-L-Lys-L-Phe-$NH_2$
H-D-Lys-L-Dmt-L-Lys-L-Phe-$NH_2$
H-Dmt-D-Arg-Lys-Phe-$NH_2$
H-Dmt-D-Arg-$NH_2$ -continued H-Dmt-D-Arg-Phe-Lys-NH₂
H-Dmt-D-Phe-Arg-Lys-NH₂
H-Dmt-Lys-D-Arg-Phe-NH₂
H-Dmt-Lys-Phe-D-Arg-NH₂
H-Dmt-Phe-D-Arg-Lys-NH₂
H-Dmt-Phe-Lys-D-Arg-NH₂
H-D-N2-acetylarginine-Dmt-Lys-Phe-NH₂
H-D-N8-acetylarginine-Dmt-Lys-Phe-NH₂
H-D-Phe-D-Arg-D-Phe-D-Lys-NH₂
H-L-Dmt-D-Arg-L-Lys-L-Phe-NH₂
H-L-Dmt-D-Arg-L-Phe-L-Lys-NH₂
H-L-Dmt-L-Lys-D-Arg-L-Phe-NH₂
H-L-Dmt-L-Lys-L-Phe-D-Arg-NH₂
H-L-Dmt-L-Phe-D-Arg-L-Lys-NH₂
H-L-Dmt-L-Phe-L-Lys-D-Arg-NH₂
H-L-His-L-Dmt-L-Lys-L-Phe-NH₂ (SEQ ID NO: 16)
H-L-Lys-D-Arg-L-Dmt-L-Phe-NH₂
H-L-Lys-D-Arg-L-Phe-L-Dmt-NH₂
H-L-Lys-L-Dmt-D-Arg-L-Phe-NH₂
H-L-Lys-L-Dmt-L-Lys-L-Phe-NH₂ (SEQ ID NO: 17)
H-L-Lys-L-Dmt-L-Phe-D-Arg-NH₂
H-L-Lys-L-Phe-D-Arg-L-Dmt-NH₂
H-L-Lys-L-Phe-L-Dmt-D-Arg-NH₂
H-L-Phe-D-Arg-L-Dmt-L-Lys-NH₂
H-L-Phe-D-Arg-L-Lys-L-Dmt-NH₂
H-L-Phe-L-Dmt-D-Arg-L-Lys-NH₂
H-L-Phe-L-Dmt-L-Lys-D-Arg-NH₂
H-L-Phe-L-Lys-D-Arg-L-Dmt-NH₂
H-L-Phe-L-Lys-L-Dmt-D-Arg-NH₂
H-Lys-D-Arg-Dmt-Phe-NH₂
H-Lys-D-Arg-Phe-Dmt-NH₂
H-Lys-Dmt-D-Arg-Phe-NH₂
H-Lys-Dmt-Phe-D-Arg-NH₂
H-Lys-D-Phe-Arg-Dmt-NH₂
H-Lys-Phe-D-Arg-Dmt-NH₂
H-Lys-Phe-Dmt-D-Arg-NH₂
H-N2-acetyl-D-arginine-L-Dmt-L-Lys-L-Phe-NH₂
H-N7-acetyl-D-arginine-Dmt-Lys-Phe-NH₂
H-Phe(d5)-D-Arg-Phe(d5)-Lys-NH₂
H-Phe-Arg-Phe-Lys-NH₂ (SEQ ID NO: 18)
H-Phe-D-Arg-Dmt-Lys-NH₂
H-Phe-D-Arg-Dmt-Lys-NH₂
H-Phe-D-Arg-D-Phe-Lys-NH₂
H-Phe-D-Arg-Lys-Dmt-NH₂
H-Phe-D-Arg-Phe-D-Lys-NH₂
H-Phe-D-Arg-Phe-Lys-Glu-Cys-Gly-NH₂
H-Phe-D-Dmt-Arg-Lys-NH₂
H-Phe-Dmt-D-Arg-Lys-NH₂
H-Phe-Dmt-Lys-D-Arg-NH₂
H-Phe-Lys-D-Arg-Dmt-NH₂
H-Phe-Lys-Dmt-D-Arg-NH₂
L-Arg-D-Dmt-D-Lys-D-Phe-NH₂
L-Arg-D-Dmt-D-Lys-D-Phe-NH₂
L-Arg-D-Dmt-D-Lys-L-Phe-NH₂
L-Arg-D-Dmt-D-Lys-L-Phe-NH₂
L-Arg-D-Dmt-L-Lys-D-Phe-NH₂
L-Arg-D-Dmt-L-Lys-D-Phe-NH₂
L-Arg-D-Dmt-L-Lys-L-Phe-NH₂
L-Arg-D-Dmt-L-Lys-L-Phe-NH₂
L-Arg-L-Dmt-D-Lys-D-Phe-NH₂
L-Arg-L-Dmt-D-Lys-D-Phe-NH₂
L-Arg-L-Dmt-D-Lys-L-Phe-NH₂
L-Arg-L-Dmt-D-Lys-L-Phe-NH₂
L-Arg-L-Dmt-L-Lys-D-Phe-NH₂
L-Arg-L-Dmt-L-Lys-D-Phe-NH₂
L-Arg-L-Dmt-L-Lys-L-Phe-NH₂ (SEQ ID NO: 19)
L-Arg-L-Dmt-L-Lys-L-Phe-NH₂ (SEQ ID NO: 19)
Lys-Dmt-Arf
Lys-Dmt-D-Arg-NH₂
Lys-Phe
Lys-Phe-Arg-Dmt (SEQ ID NO: 10)
Lys-Phe-NH₂
Lys-Trp-Arg
Lys-Trp-D-Arg-NH₂
Phe-Arg-Dmt-Lys (SEQ ID NO: 11)
Phe-Arg-Phe-Lys (SEQ ID NO: 12)
Phe-Arg-Phe-Lys (SEQ ID NO: 12)
Phe-Arg-Phe-Lys (SEQ ID NO: 12)
Phe-Arg-Phe-Lys (SEQ ID NO: 12)

-continued

Phe-Arg-Phe-Lys (SEQ ID NO: 12)
Phe-Arg-Phe-Lys-Glu-Cys-Gly (SEQ ID NO: 13)
Phe-Dmt-Arg-Lys (SEQ ID NO: 14)
Phe-Lys-Dmt
Phe-Lys-Dmt-NH₂
Succinic monoester CoQ0-Phe-D-Arg-Phe-Lys-NH₂ wherein Cha is cyclohexylalanine.

In some aspects, a kit for the detection of aromatic-cationic peptides is provided. In some embodiments, the kits include a biological sample collector to collect a sample from the subject, and a sample storage device for preservation of the biological sample. In some embodiments, the biological sample comprises a fluid. In some embodiments, the biological sample comprises a cell. In some embodiments, the biological sample comprises a tissue sample. In some embodiments, the biological sample comprises a biopsy.

DETAILED DESCRIPTION

It is to be appreciated that certain aspects, modes, embodiments, variations and features of the invention are described below in various levels of detail in order to provide a substantial understanding of the present invention.

In practicing the present invention, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N Y, 1989); *DNA Cloning: A Practical Approach*, Vols. I and II, Glover, Ed. (1985); *Oligonucleotide Synthesis*, Gait, Ed. (1984); Nucleic Acid Hybridization, *Hames & Higgins, Eds.* (1985); Transcription and Translation, *Hames & Higgins, Eds.* (1984); *Animal Cell Culture, Freshney, Ed.* (1986); Immobilized Cells and Enzymes (IRL Press, 1986); Perbal, *A Practical Guide to Molecular Cloning*; the series, *Meth. Enzymol.*, (Academic Press, Inc., 1984); Gene Transfer Vectors for Mammalian Cells, Miller & Calos, Eds. (Cold Spring Harbor Laboratory, N Y, 1987); and *Meth. Enzymol.*, Vols. 154 and 155, Wu & Grossman, and Wu, Eds., respectively.

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "biological sample" refers to material derived from or contacted by living cells. The term encompasses tissues, cells and biological fluids isolated from a subject, as well as tissues, cells and fluids present within a subject. Biological samples include but are not limited to, whole blood, fractionated blood, semen, saliva, tears, urine, fecal material, sweat, buccal, skin, cerebrospinal fluid, and hair. Biological samples also includes biopsies of internal organs and cancers. Biological samples can be obtained from subjects for diagnosis or research or can be obtained from undiseased individuals, as controls or for basic research.

As used herein, the term "effective amount" refers to a quantity sufficient to achieve a desired therapeutic and/or prophylactic effect. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the terms "polypeptide", "peptide", and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the terms "treating" or "treatment" or "alleviation" refers to both therapeutic treatment and prophylactic or preventative measures, wherein the object is to prevent or slow down (lessen) the targeted pathologic condition or disorder. It is also to be appreciated that the various modes of treatment or prevention of medical conditions as described are intended to mean "substantial", which includes total but also less than total treatment or prevention, and wherein some biologically or medically relevant result is achieved.

As used herein, "prevention" or "preventing" of a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

Methods of Prevention or Treatment

The present technology relates to the treatment or prevention of disease by administration of certain aromatic-cationic peptides.

The aromatic-cationic peptides are water-soluble and highly polar. Despite these properties, the peptides can readily penetrate cell membranes. The aromatic-cationic peptides typically include a minimum of two or three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, more preferably about nine, and most preferably about six.

The amino acids of the aromatic-cationic peptides can be any amino acid. As used herein, the term "amino acid" is used to refer to any organic molecule that contains at least one amino group and at least one carboxyl group. Typically, at least one amino group is at the a position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid includes hydroxyproline (Hyp).

The peptides optionally contain one or more non-naturally occurring amino acids. Optimally, the peptide has no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are preferably resistant, and more preferably insensitive, to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, preferably less than four, more preferably less than three, and most preferably, less than two contiguous L-amino acids recognized by common proteases, irrespective of whether the amino acids are naturally or non-naturally occurring. Optimally, the peptide has only D-amino acids, and no L-amino acids. If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the peptide is defined by formula I:

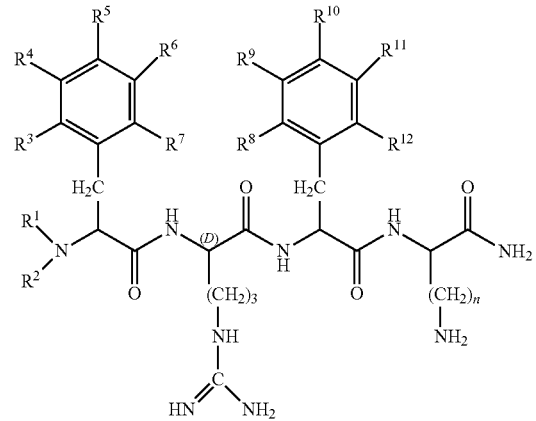

wherein $R^1$ and $R^2$ are each independently selected from
(i) hydrogen;
(ii) linear or branched $C_1$-$C_6$ alkyl;
(iii)

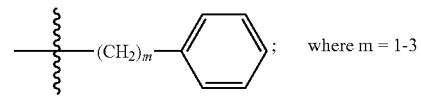; where m = 1-3

(iv)

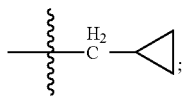

(v)

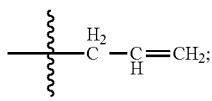

$R^3$, $R^4$, $R^5$, $R^6$, $R^7$, $R^8$, $R^9$, $R^{10}$, $R^{11}$ and $R^{12}$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo; and n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

In one embodiment, the peptide is defined by formula II:

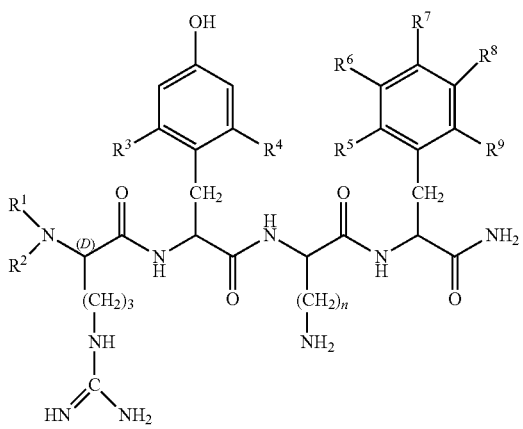

wherein $R^1$ and $R^2$ are each independently selected from
  (i) hydrogen;
  (ii) linear or branched $C_1$-$C_6$ alkyl;
  (iii)

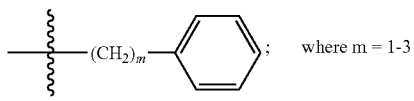

(iv)

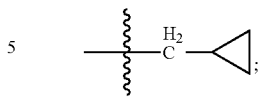

(v)

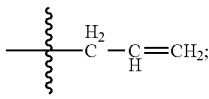

$R^3$ and $R^4$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo;

$R^5$, $R^6$, $R^7$, $R^8$, and R' are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo; and n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In one embodiment, the aromatic-cationic peptides have a core structural motif of alternating aromatic and cationic amino acids. Fr example, the peptide may be a tetrapeptide defined by any of formulas III to VI set forth below:

| | |
|---|---|
| Aromatic-Cationic-Aromatic-Cationic | (Formula III) |
| Cationic-Aromatic-Cationic-Aromatic | (Formula IV) |
| Aromatic-Aromatic-Cationic-Cationic | (Formula V) |
| Cationic-Cationic-Aromatic-Aromatic | (Formula VI) | wherein, Aromatic is a residue selected from the group consisting of: Phe (F), Tyr (Y), Trp (W), and Cyclohexyl-alanine (Cha); and Cationic is a residue selected from the group consisting of: Arg (R), Lys (K), Norleucine (Nle), and 2-amino-heptanoic acid (Ahe).

In one aspect, the disclosure provides a method of reducing the number of mitochondria undergoing mitochondrial permeability transition (MPT), or preventing mitochondrial permeability transitioning in a mammal in need thereof, the method comprising administering to the mammal an effective amount of one or more aromatic-cationic peptides described herein. In another aspect, the disclosure provides a method for increasing the ATP synthesis rate in a mammal in need thereof, the method comprising administering to the mammal an effective amount of one or more aromatic-cationic peptides described herein. In yet another aspect, the disclosure provides a method for reducing oxidative damage in a mammal in need thereof, the method comprising administering to the mammal an effective amount of one or more aromatic-cationic peptides described herein.

In one embodiment, the aromatic-cationic peptides have a relationship between the minimum number of net positive charges at physiological pH ($p_m$) and the total number of amino acid residues (r) wherein 3 $p_m$ is the largest number that is less than or equal to r+1. In this embodiment, the relationship between the minimum number of net positive charges ($p_m$) and the total number of amino acid residues (r) is as follows:

TABLE 1

Amino acid number and net positive charges ($3p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein 2 $p_m$ is the largest number that is less than or equal to r+1. In this embodiment, the relationship between the minimum number of net positive charges ($p_m$) and the total number of amino acid residues (r) is as follows:

TABLE 2

Amino acid number and net positive charges ($2p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, suitably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges ($3a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t+1$. In this embodiment, the relationship between the minimum number of aromatic amino acid residues (a) and the total number of net positive charges ($p_t$) is as follows:

TABLE 4

Aromatic groups and net positive charges (2a ≤ $p_t$ + 1 or a = $p_t$ = 1)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal. In one embodiment, the aromatic-cationic peptide may have
 (a) at least one net positive charge;
 (b) a minimum of three amino acids;
 (c) a maximum of about twenty amino acids;
 (d) a relationship between the minimum number of net positive charges ($p_m$) and the total number of amino acid residues (r) wherein 3 $p_m$ is the largest number that is less than or equal to r+1; and
 (e) a relationship between the minimum number of aromatic groups (a) and the total number of net positive charges ($p_t$) wherein 3a is the largest number that is less than or equal to $p_t+1$, except that when a is 1, $p_t$ may also be 1.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

Aromatic-cationic peptides include, but are not limited to, the following exemplary peptides:

6-Butyric acid CoQ0-Phe-D-Arg-Phe-Lys-NH$_2$
6-Decanoic acid CoQ0-Phe-D-Arg-Phe-Lys-NH$_2$
Arg-Arg-Dmt-Phe (SEQ ID NO: 1)
Arg-Cha-Lys
Arg-Dmt
Arg-Dmt-Arg
Arg-Dmt-Lys
Arg-Dmt-Lys-Phe (SEQ ID NO: 2)
Arg-Dmt-Lys-Phe-Cys (SEQ ID NO: 3)
Arg-Dmt-Phe
Arg-Dmt-Phe-Lys (SEQ ID NO: 4)
Arg-Lys-Dmt-Phe (SEQ ID NO: 5)
Arg-Lys-Phe-Dmt (SEQ ID NO: 6)
Arg-Phe-Dmt-Lys (SEQ ID NO: 7)
Arg-Phe-Lys -continued Arg-Trp-Lys
Arg-Tyr-Lys
Arg-Tyr-Lys-Phe (SEQ ID NO: 8)
D-Arg-D-Dmt-D-Lys-D-Phe-NH$_2$ -continued D-Arg-D-Dmt-D-Lys-L-Phe-NH$_2$
D-Arg-D-Dmt-L-Lys-D-Phe-NH$_2$
D-Arg-D-Dmt-L-Lys-L-Phe-NH$_2$
D-Arg-Dmt-D-Lys- NH$_2$
D-Arg-Dmt-D-Lys-Phe-NH$_2$
D-Arg-Dmt-Lys-D-Phe-NH$_2$
D-Arg-Dmt-Lys-NH$_2$
D-Arg-Dmt-Lys-Phe-Cys
D-Arg-Dmt-NH$_2$
D-Arg-L-Dmt-D-Lys-D-Phe-NH$_2$
D-Arg-L-Dmt-D-Lys-L-Phe-NH$_2$
D-Arg-L-Dmt-L-Lys-D-Phe-NH$_2$
D-Arg-Phe-Lys-NH$_2$
D-Arg-Trp-Lys-NH$_2$
D-Arg-Tyr-Lys-NH$_2$
Dmt-Arg
Dmt-Lys
Dmt-Lys-D-Phe-NH$_2$
Dmt-Lys-NH$_2$
Dmt-Lys-Phe
Dmt-Lys-Phe
Dmt-Lys-Phe-NH$_2$
Dmt-Phe-Arg-Lys (SEQ ID NO: 9)
H-Arg-D-Dmt-Arg-NH$_2$
H-Arg-D-Dmt-Lys-NH$_2$
H-Arg-D-Dmt-Lys-Phe-NH$_2$
H-Arg-D-Dmt-NH$_2$
H-Arg-Dmt-Lys-Phe-NH$_2$ (SEQ ID NO: 15)
H-D-Arg-2,6-dichloro-L-tyrosine-L-Lys-L-Phe-NH$_2$
H-D-Arg-2,6-dichlorotyrosine-Lys-Phe-NH$_2$
H-D-Arg-2,6-difluoro-L-tyrosine-L-Lys-L-Phe-NH$_2$
H-D-Arg-2,6-difluorotyrosine-Lys-Phe-NH$_2$
H-D-Arg-2,6-dimethyl-L-phenylalanine-L-Lys-L-Phe-NH$_2$
H-D-Arg-2,6-dimethylphenylalanine-Lys-Phe-NH$_2$
H-D-Arg-4-methoxy-2,6-dimethyl-L-tyrosine-L-Lys-L-Phe-NH$_2$
H-D-Arg-4-methoxy-2,6-dimethyltyrosine-Lys-Phe-NH$_2$
H-D-Arg-Arg-Dmt-Phe-NH$_2$
H-D-Arg-Cha-Lys-NH$_2$
H-D-Arg-D-Dmt-D-Lys-D-Phe-NH$_2$
H-D-Arg-D-Dmt-Lys-Phe-NH$_2$
H-D-Arg-D-Dmt-NH$_2$
H-D-Arg-Dmt-D-Lys-D-Phe-NH$_2$
H-D-Arg-Dmt-Lys-2,6-dimethylphenylalanine-NH$_2$
H-D-Arg-Dmt-Lys-3-hydroxyphenylalanine-NH$_2$
H-D-Arg-Dmt-Lys-NH$_2$
H-D-Arg-Dmt-Lys-OH
H-D-Arg-Dmt-Lys-Phe-OH
H-D-Arg-Dmt-N6-acetyllysine-Phe-NH$_2$
H-D-Arg-Dmt-OH
H-D-Arg-Dmt-Phe-Lys-NH$_2$
H-D-Arg-Dmt-Phe-NH$_2$
H-D-Arg-D-Phe-L-Lys-L-Phe-NH$_2$
H-D-Arg-D-Trp-L-Lys-L-Phe-NH$_2$
H-D-Arg-D-Tyr-L-Lys-L-Phe-NH$_2$
H-D-Arg-L-Dmt-L-Lys-2,6-dimethyl-L-phenylalanine-NH$_2$
H-D-Arg-L-Dmt-L-Lys-3-hydroxy-L-phenylalanine-NH$_2$
H-D-Arg-L-Dmt-L-Lys-D-Dmt-NH$_2$
H-D-Arg-L-Dmt-L-Lys-D-Trp-NH$_2$
H-D-Arg-L-Dmt-L-Lys-D-Tyr-NH$_2$
H-D-Arg-L-Dmt-L-Lys-L-Dmt-NH$_2$ H-D-Arg-L-Dmt-L-Lys-L-Dmt-NH₂
H-D-Arg-L-Dmt-L-Lys-L-Trp-NH₂
H-D-Arg-L-Dmt-L-Lys-L-Tyr-NH₂
H-D-Arg-L-Dmt-L-Phe-L-Lys-NH₂
H-D-Arg-L-Dmt-N6-acetyl-L-lysine-L-Phe-NH₂
H-D-Arg-L-Lys-L-Dmt-L-Phe-NH₂
H-D-Arg-L-Lys-L-Phe-L-Dmt-NH₂
H-D-Arg-L-Phe-L-Dmt-L-Lys-NH₂
H-D-Arg-L-Phe-L-Lys-L-Dmt-NH₂
H-D-Arg-L-Phe-L-Lys-L-Phe-NH₂
H-D-Arg-L-Trp-L-Lys-L-Phe-NH₂
H-D-Arg-L-Tyr-L-Lys-L-Phe-NH₂
H-D-Arg-Lys-Dmt-Phe-NH₂
H-D-Arg-Lys-Phe-Dmt-NH₂
H-D-Arg-Phe-Dmt-Lys-NH₂
H-D-Arg-Phe-Lys-Dmt-NH₂
H-D-Arg-Tyr-Lys-Phe-NH₂
H-D-Dmt-Arg-NH₂
H-D-His-L-Dmt-L-Lys-L-Phe-NH₂
H-D-Lys-L-Dmt-L-Lys-L-Phe-NH₂
H-Dmt-D-Arg-Lys-Phe-NH₂
H-Dmt-D-Arg-NH₂
H-Dmt-D-Arg-Phe-Lys-NH₂
H-Dmt-D-Phe-Arg-Lys-NH₂
H-Dmt-Lys-D-Arg-Phe-NH₂
H-Dmt-Lys-Phe-D-Arg-NH₂
H-Dmt-Phe-D-Arg-Lys-NH₂
H-Dmt-Phe-Lys-D-Arg-NH₂
H-D-N2-acetylarginine-Dmt-Lys-Phe-NH₂
H-D-N8-acetylarginine-Dmt-Lys-Phe-NH₂
H-D-Phe-D-Arg-D-Phe-D-Lys-NH₂
H-L-Dmt-D-Arg-L-Lys-L-Phe-NH₂
H-L-Dmt-D-Arg-L-Phe-L-Lys-NH₂
H-L-Dmt-L-Lys-D-Arg-L-Phe-NH₂
H-L-Dmt-L-Lys-L-Phe-D-Arg-NH₂
H-L-Dmt-L-Phe-D-Arg-L-Lys-NH₂
H-L-Dmt-L-Phe-L-Lys-D-Arg-NH₂
H-L-His-L-Dmt-L-Lys-L-Phe-NH₂ (SEQ ID NO: 16)
H-L-Lys-D-Arg-L-Dmt-L-Phe-NH₂
H-L-Lys-D-Arg-L-Phe-L-Dmt-NH₂
H-L-Lys-L-Dmt-D-Arg-L-Phe-NH₂
H-L-Lys-L-Dmt-L-Lys-L-Phe-NH₂ (SEQ ID NO: 17)
H-L-Lys-L-Dmt-L-Phe-D-Arg-NH₂
H-L-Lys-L-Phe-D-Arg-L-Dmt-NH₂
H-L-Lys-L-Phe-L-Dmt-D-Arg-NH₂
H-L-Phe-D-Arg-L-Dmt-L-Lys-NH₂
H-L-Phe-D-Arg-L-Lys-L-Dmt-NH₂
H-L-Phe-L-Dmt-D-Arg-L-Lys-NH₂
H-L-Phe-L-Dmt-L-Lys-D-Arg-NH₂
H-L-Phe-L-Lys-D-Arg-L-Dmt-NH₂
H-L-Phe-L-Lys-L-Dmt-D-Arg-NH₂
H-Lys-D-Arg-Dmt-Phe-NH₂
H-Lys-D-Arg-Phe-Dmt-NH₂
H-Lys-Dmt-D-Arg-Phe-NH₂
H-Lys-Dmt-Phe-D-Arg-NH₂
H-Lys-D-Phe-Arg-Dmt-NH₂
H-Lys-Phe-D-Arg-Dmt-NH₂
H-Lys-Phe-Dmt-D-Arg-NH₂
H-N2-acetyl-D-arginine-L-Dmt-L-Lys-L-Phe-NH₂
H-N7-acetyl-D-arginine-Dmt-Lys-Phe-NH₂
H-Phe(d5)-D-Arg-Phe(d5)-Lys-NH₂
H-Phe-Arg-Phe-Lys-NH₂ (SEQ ID NO: 18)
H-Phe-D-Arg-Dmt-Lys-NH₂
H-Phe-D-Arg-Dmt-Lys-NH₂
H-Phe-D-Arg-D-Phe-Lys-NH₂
H-Phe-D-Arg-Lys-Dmt-NH₂
H-Phe-D-Arg-Phe-D-Lys-NH₂
H-Phe-D-Arg-Phe-Lys-Glu-Cys-Gly-NH₂
H-Phe-D-Dmt-Arg-Lys-NH₂
H-Phe-Dmt-D-Arg-Lys-NH₂
H-Phe-Dmt-Lys-D-Arg-NH₂
H-Phe-Lys-D-Arg-Dmt-NH₂
H-Phe-Lys-Dmt-D-Arg-NH₂
L-Arg-D-Dmt-D-Lys-D-Phe-NH₂
L-Arg-D-Dmt-D-Lys-D-Phe-NH₂
L-Arg-D-Dmt-D-Lys-L-Phe-NH₂
L-Arg-D-Dmt-D-Lys-L-Phe-NH₂
L-Arg-D-Dmt-L-Lys-D-Phe-NH₂
L-Arg-D-Dmt-L-Lys-D-Phe-NH₂
L-Arg-D-Dmt-L-Lys-L-Phe-NH₂
L-Arg-D-Dmt-L-Lys-L-Phe-NH₂
L-Arg-L-Dmt-D-Lys-D-Phe-NH₂
L-Arg-L-Dmt-D-Lys-D-Phe-NH₂
L-Arg-L-Dmt-D-Lys-L-Phe-NH₂
L-Arg-L-Dmt-D-Lys-L-Phe-NH₂
L-Arg-L-Dmt-L-Lys-D-Phe-NH₂
L-Arg-L-Dmt-L-Lys-D-Phe-NH₂
L-Arg-L-Dmt-L-Lys-L-Phe-NH₂ (SEQ ID NO: 19)
L-Arg-L-Dmt-L-Lys-L-Phe-NH₂ (SEQ ID NO: 19)
Lys-Dmt-Arf
Lys-Dmt-D-Arg-NH₂
Lys-Phe
Lys-Phe-Arg-Dmt (SEQ ID NO: 10)
Lys-Phe-NH₂
Lys-Trp-Arg
Lys-Trp-D-Arg-NH₂
Phe-Arg-Dmt-Lys (SEQ ID NO: 11)
Phe-Arg-Phe-Lys (SEQ ID NO: 12)
Phe-Arg-Phe-Lys (SEQ ID NO: 12)
Phe-Arg-Phe-Lys (SEQ ID NO: 12)
Phe-Arg-Phe-Lys (SEQ ID NO: 12)
Phe-Arg-Phe-Lys (SEQ ID NO: 12)
Phe-Arg-Phe-Lys-Glu-Cys-Gly (SEQ ID NO: 13)
Phe-Dmt-Arg-Lys (SEQ ID NO: 14)
Phe-Lys-Dmt
Phe-Lys-Dmt-NH₂
Succinic monoester CoQ0-Phe-D-Arg-Phe-Lys-NH₂ wherein Cha is cyclohexylalanine.

In one embodiment, the peptides have mu-opioid receptor agonist activity (i.e., they activate the mu-opioid receptor). Mu-opioid activity can be assessed by radioligand binding to cloned mu-opioid receptors or by bioassays using the guinea pig ileum (Schiller et al., *Eur J Med Chem,* 35:895-901, 2000; Zhao et al., *J Pharmacol Exp Ther,* 307:947-954, 2003). Activation of the mu-opioid receptor typically elicits an analgesic effect. In certain instances, an aromatic-cationic peptide having mu-opioid receptor agonist activity is preferred. For example, during short-term treatment, such as in an acute disease or condition, it may be beneficial to use an aromatic-cationic peptide that activates the mu-opioid receptor. Such acute diseases and conditions are often associated with moderate or severe pain. In these instances, the analgesic effect of the aromatic-cationic peptide may be beneficial in the treatment regimen of the human patient or other mammal. An aromatic-cationic peptide which does not activate the mu-opioid receptor, however, may also be used with or without an analgesic, according to clinical requirements. Peptides which have mu-opioid receptor agonist activity are typically those peptides which have a tyrosine residue or a tyrosine derivative at the N-terminus (i.e., the first amino acid position).

Alternatively, in other instances, an aromatic-cationic peptide that does not have mu-opioid receptor agonist activity is preferred. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment. Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N,2',6'-trimethylphenylalanine (Tmp), and 2'-hydroxy-6'-methylphenylalanine (Hmp).

The peptides mentioned herein and their derivatives can further include functional variants. A peptide is considered a functional variant if the variant has the same function as the stated peptide. The analog may, for example, be a substitution variant of a peptide, wherein one or more amino acids are substituted by another amino acid. Suitable substitution variants of the peptides include conservative amino acid substitutions. Amino acids may be grouped according to their physicochemical characteristics as follows:
 (a) Non-polar amino acids: Ala(A) Ser(S) Thr(T) Pro(P) Gly(G) Cys (C);
 (b) Acidic amino acids: Asn(N) Asp(D) Glu(E) Gln(Q);
 (c) Basic amino acids: His(H) Arg(R) Lys(K);
 (d) Hydrophobic amino acids: Met(M) Leu(L) Ile(I) Val (V); and
 (e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide.

In some embodiments, the peptides disclosed herein are derived from precursors, such as peptide precursors. For example, in some embodiments, the precursor comprises an aromatic-cationic which is also a therapeutic agent or drug.

Synthesis of Aromatic-Cationic Peptides

The aromatic-cationic peptides disclosed herein may be synthesized by any of the methods well known in the art. Suitable methods for chemically synthesizing the protein include, for example, liquid phase and solid phase synthesis, and those methods described by Stuart and Young in Solid Phase Peptide Synthesis, Second Edition, Pierce Chemical Company (1984), and in *Methods Enzymol.*, 289, Academic Press, Inc, New York (1997). Recombinant peptides may be generated using conventional techniques in molecular biology, protein biochemistry, cell biology, and microbiology, such as those described in *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N Y, 1989); *DNA Cloning: A Practical Approach*, Vols. I and II, Glover, Ed. (1985); *Oligonucleotide Synthesis*, Gait, Ed. (1984); Nucleic Acid Hybridization, *Hames & Higgins, Eds.* (1985); Transcription and Translation, *Hames & Higgins, Eds.* (1984); *Animal Cell Culture, Freshney, Ed.* (1986); Immobilized Cells and Enzymes (IRL Press, 1986); Perbal, *A Practical Guide to Molecular Cloning*; the series, *Meth. Enzymol.*, (Academic Press, Inc., 1984); Gene Transfer Vectors for Mammalian Cells, Miller & Calos, Eds. (Cold Spring Harbor Laboratory, N Y, 1987); and *Meth. Enzymol.*, Vols. 154 and 155, Wu & Grossman, and Wu, Eds., respectively.

Detection and Characterization of Aromatic-Cationic Peptides

The aromatic-cationic peptides described herein may be detected and/or characterized using methods known in the art. Peptides in a sample may be detected, for example, using methods of high performance liquid chromatography (HPLC) such as those described in Aguilar, *HPLC of Peptides and Proteins: Methods and Protocols*, Humana Press, New Jersey (2004). Peptides may be detected, for example, using reverse-phase HPLC (RP-HPLC) or ion exchange HPLC. High-performance liquid chromatography (or high-pressure liquid chromatography, HPLC) is a chromatographic technique that can separate a mixture of compounds and is used in biochemistry and analytical chemistry to identify, quantify and purify the individual components of the mixture. HPLC typically utilizes different types of stationary phases, a pump that moves the mobile phase(s) and analyte through the column, and a detector to provide a characteristic retention time for the analyte. The detector may also provide additional information related to the analyte, (e.g., UV/Vis spectroscopic data for analyte if so equipped). Analyte retention time varies depending on the strength of its interactions with the stationary phase, the ratio/composition of solvent(s) used, and the flow rate of the mobile phase. Typically, with HPLC, a pump (rather than gravity) provides the higher pressure required to move the mobile phase and analyte through a relatively densely packed column. The increased density arises from smaller particle sizes. This allows for a better separation on columns of shorter length when compared to ordinary column chromatography.

In some embodiments, peptides are detected and/or characterized using reverse phase HPLC (RP-HPLC). Reversed phase HPLC (RP-HPLC or RPC) typically includes a non-polar stationary phase and an aqueous, moderately polar mobile phase. One common stationary phase is a silica which has been treated with RMe2SiCl, where R is a straight chain alkyl group such as $C_{18}H_{37}$ or $C_8H_{17}$. With these stationary phases, retention time is longer for molecules which are less polar, while polar molecules elute more readily.

In some embodiments, peptides are detected and/or characterized using ion exchange HPLC. Typically, in ion-exchange chromatography, retention is based on the attraction between solute ions and charged sites bound to the stationary phase. Ions of the same charge are excluded. Typical types of ion exchangers include but are not limited to the following. Polystyrene resins. These resins allow cross linkage which increases the stability of the chain. In general, higher cross linkage reduces swerving, which increases the equilibration time and ultimately improves selectivity. Cellulose and dextran ion exchangers (gels): These possess larger pore sizes and low charge densities making them suitable for protein separation. Controlled-pore glass or porous silica.

In general, ion exchangers favor the binding of ions of higher charge and smaller radius. Typically, an increase in counter ion (with respect to the functional groups in resins) concentration reduces the retention time. Typically, an increase in pH reduces the retention time in cation exchange while a decrease in pH reduces the retention time in anion exchange.

In addition, peptides in a sample may be characterized, for example, using methods of mass spectrometry (MS). A general reference related to methods of mass spectrometry is Sparkman, *Mass Spectrometry Desk Reference*, Pittsburgh: Global View Pub (2000).

One of skill in the art will understand that the aromatic-cationic peptides described herein may be detected and/or characterized using any number of conventional biochemical methods known in the art. The HPLC and MS methods described herein are illustrative and are not to be construed as limiting in any way.

Prophylactic and Therapeutic Uses of Aromatic-Cationic Peptides

The aromatic-cationic peptides described herein are useful to prevent or treat disease. Specifically, the disclosure provides for both prophylactic and therapeutic methods of treating a subject at risk of (or susceptible to) disease by administering the aromatic-cationic peptides described herein. Accordingly, the present methods provide for the prevention and/or treatment of disease in a subject by administering an effective amount of an aromatic-cationic peptide to a subject in need thereof.

In one embodiment, the peptides described above are useful in treating any disease or condition that is associated with mitochondrial permeability transition (MPT). Reducing the number of mitochondria undergoing, and preventing, MPT is important, since MPT is associated with several common diseases and conditions in mammals. Such diseases and conditions include, but are not limited to, ischemia and/or reperfusion of a tissue or organ, hypoxia, neurodegenerative diseases, etc. Mammals in need of treatment or prevention of MPT are those mammals suffering from these diseases or conditions.

Ischemia in a tissue or organ of a mammal is a multifaceted pathological condition which is caused by oxygen deprivation (hypoxia) and/or glucose (e.g., substrate) deprivation. Oxygen and/or glucose deprivation in cells of a tissue or organ leads to a reduction or total loss of energy generating capacity and consequent loss of function of active ion transport across the cell membranes. Oxygen and/or glucose deprivation also leads to pathological changes in other cell membranes, including permeability transition in the mitochondrial membranes. In addition other molecules, such as apoptotic proteins normally compartmentalized within the mitochondria, may leak out into the cytoplasm and cause apoptotic cell death. Profound ischemia can lead to necrotic cell death. Ischemia or hypoxia in a particular tissue or organ may be caused by a loss or severe reduction in blood supply to the tissue or organ. The loss or severe reduction in blood supply may, for example, be due to thromboembolic stroke, coronary atherosclerosis, or peripheral vascular disease. The tissue affected by ischemia or hypoxia is typically muscle, such as cardiac, skeletal, or smooth muscle. The organ affected by ischemia or hypoxia may be any organ that is subject to ischemia or hypoxia. Examples of organs affected by ischemia or hypoxia include brain, heart, kidney, and prostate. For instance, cardiac muscle ischemia or hypoxia is commonly caused by atherosclerotic or thrombotic blockages which lead to the reduction or loss of oxygen delivery to the cardiac tissues by the cardiac arterial and capillary blood supply. Such cardiac ischemia or hypoxia may cause pain and necrosis of the affected cardiac muscle, and ultimately may lead to cardiac failure. Ischemia or hypoxia in skeletal muscle or smooth muscle may arise from similar causes. For example, ischemia or hypoxia in intestinal smooth muscle or skeletal muscle of the limbs may also be caused by atherosclerotic or thrombotic blockages.

Reperfusion is the restoration of blood flow to any organ or tissue in which the flow of blood is decreased or blocked. For example, blood flow can be restored to any organ or tissue affected by ischemia or hypoxia. The restoration of blood flow (reperfusion) can occur by any method known to those in the art. For instance, reperfusion of ischemic cardiac tissues may arise from angioplasty, coronary artery bypass graft, or the use of thrombolytic drugs.

The methods described herein can also be used in the treatment or prophylaxis of neurodegenerative diseases associated with MPT. Neurodegenerative diseases associated with MPT include, for instance, Parkinson's disease, Alzheimer's disease, Huntington's disease and Amyotrophic Lateral Sclerosis (ALS, also known as Lou Gherig's disease). The methods disclosed herein can be used to delay the onset or slow the progression of these and other neurodegenerative diseases associated with MPT. The methods disclosed herein are particularly useful in the treatment of humans suffering from the early stages of neurodegenerative diseases associated with MPT and in humans predisposed to these diseases.

The aromatic-cationic peptides described above are also useful in preventing or treating insulin resistance, metabolic syndrome, burn injuries and secondary complications, heart failure, diabetic complications (such as diabetic retinopathy), ophthalmic conditions (such as choroidal neovascularization, retinal degeneration, and oxygen-induced retinopathy).

The aromatic-cationic peptides described above are also useful in reducing oxidative damage in a mammal in need thereof. Mammals in need of reducing oxidative damage are those mammals suffering from a disease, condition or treatment associated with oxidative damage. Typically, the oxidative damage is caused by free radicals, such as reactive oxygen species (ROS) and/or reactive nitrogen species (RNS). Examples of ROS and RNS include hydroxyl radical (HO$^-$), superoxide anion radical (O$_2^-$), nitric oxide (NO$^-$), hydrogen peroxide (H$_2$O$_2$), hypochlorous acid (HOCl) and peroxynitrite anion (ONOO$^-$). In one embodiment, a mammal in need thereof may be a mammal undergoing a treatment associated with oxidative damage. For example, the mammal may be undergoing reperfusion, ischemia, or hypoxia.

In another embodiment, the aromatic-cationic peptides can be used to prevent lipid peroxidation and/or inflammatory processes that are associated with oxidative damage for a disease or condition. Lipid peroxidation refers to oxidative modification of lipids. The lipids can be present in the membrane of a cell. This modification of membrane lipids typically results in change and/or damage to the membrane function of a cell. In addition, lipid peroxidation can also occur in lipids or lipoproteins exogenous of a cell. For example, low-density lipoproteins are susceptible to lipid peroxidation. An example of a condition associated with lipid peroxidation is atherosclerosis. Reducing oxidative damage associated with atherosclerosis is important since atherosclerosis is implicated in, for example, heart attacks and coronary artery disease.

Inflammatory processes include and activation of the immune system. Typically, the immune system is activated by an antigenic substance. The antigenic substance can be any substance recognized by the immune system, and include self-derived particles and foreign-derived particles. Examples of diseases or conditions occurring from an inflammatory process to self-derived particles include arthritis and multiple sclerosis. Examples of foreign particles include viruses and bacteria. The virus can be any virus which activates an inflammatory process, and associated with oxidative damage. Examples of viruses include, hepatitis A, B or C virus, human immunodeficiency virus, influenza virus, and bovine diarrhea virus. For example, hepatitis virus can elicit an inflammatory process and formation of free radicals, thereby damaging the liver. The bacteria can be any bacteria, and include gram-negative or gram-positive bacteria. Gram-negative bacteria contain lipopolysaccharide in the bacteria wall. Examples of gram-negative bacteria include *Escherichia coli, Klebsiella pneumoniae, Proteus species, Pseudomonas aeruginosa, Serratia,* and *Bacteroides*. Examples of gram-positive bacteria include pneumococci and streptococci. An example of an inflammatory process associated with oxidative stress caused by a bacteria is sepsis. Typically, sepsis occurs when gram-negative bacteria enter the bloodstream.

Liver damage caused by a toxic agent is another condition associated with an inflammatory process and oxidative stress. The toxic agent can be any agent which causes damage to the liver. For example, the toxic agent can cause apoptosis and/or necrosis of liver cells. Examples of such agents include alcohol, and medication, such as prescription and non-prescription drugs taken to treat a disease or condition.

The methods disclosed herein can also be used in reducing oxidative damage associated with any neurodegenerative disease or condition. The neurodegenerative disease can affect any cell, tissue or organ of the central and peripheral nervous system. Examples of such cells, tissues and organs include, the brain, spinal cord, neurons, ganglia, Schwann cells, astrocytes, oligodendrocytes and microglia. The neurodegenerative condition can be an acute condition, such as a stroke or a traumatic brain or spinal cord injury. In another embodiment, the neurodegenerative disease or condition can be a chronic neurodegenerative condition. In a chronic neurodegenerative condition, the free radicals can, for example, cause damage to a protein. An example of such a protein is amyloid .beta.-protein. Examples of chronic neurodegenerative diseases associated with damage by free radicals include Parkinson's disease, Alzheimer's disease, Huntington's disease and Amyotrophic Lateral Sclerosis (also known as Lou Gherig's disease).

Determination of the Biological Effect of the Aromatic-Cationic Peptide-Based Therapeutic. In various embodiments, suitable in vitro or in vivo assays are performed to determine the effect of a specific aromatic-cationic peptide-based therapeutic and whether its administration is indicated for treatment. In various embodiments, in vitro assays can be performed with representative animal models, to determine if a given aromatic-cationic peptide-based therapeutic exerts the desired effect in preventing or treating a disease or medical condition. Compounds for use in therapy can be tested in suitable animal model systems including, but not limited to rats, mice, chicken, pigs, cows, monkeys, rabbits, and the like, prior to testing in human subjects. Similarly, for in vivo testing, any of the animal model systems known in the art can be used prior to administration to human subjects.

Prophylactic Methods. In one aspect, the invention provides a method for preventing, in a subject, disease by administering to the subject an aromatic-cationic peptide that prevents the initiation or progression of the condition. In prophylactic applications, pharmaceutical compositions or medicaments of aromatic-cationic peptides are administered to a subject susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. Administration of a prophylactic aromatic-cationic can occur prior to the manifestation of symptoms characteristic of the aberrancy, such that a disease or disorder is prevented or, alternatively, delayed in its progression. The appropriate compound can be determined based on screening assays described above.

Therapeutic Methods. Another aspect of the technology includes methods of treating disease in a subject for therapeutic purposes. In therapeutic applications, compositions or medicaments are administered to a subject suspected of, or already suffering from such a disease in an amount sufficient to cure, or at least partially arrest, the symptoms of the disease, including its complications and intermediate pathological phenotypes in development of the disease. As such, the invention provides methods of treating an individual afflicted with a disease or medical condition.

Modes of Administration and Effective Dosages

Any method known to those in the art for contacting a cell, organ or tissue with a peptide may be employed. Suitable methods include in vitro, ex vivo, or in vivo methods. In vivo methods typically include the administration of an aromatic-cationic peptide, such as those described above, to a mammal, suitably a human. When used in vivo for therapy, the aromatic-cationic peptides are administered to the subject in effective amounts (i.e., amounts that have desired therapeutic effect). The dose and dosage regimen will depend upon the degree of the injury in the subject, the characteristics of the particular aromatic-cationic peptide used, e.g., its therapeutic index, the subject, and the subject's history.

The effective amount may be determined during pre-clinical trials and clinical trials by methods familiar to physicians and clinicians. An effective amount of a peptide useful in the methods may be administered to a mammal in need thereof by any of a number of well-known methods for administering pharmaceutical compounds. The peptide may be administered systemically or locally.

The peptide may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt comprises trifluoroacetate salt or acetate salt.

The aromatic-cationic peptides described herein or a pharmaceutically salt thereof such as acteate salt or trifluoroacetate salt, can be incorporated into pharmaceutical compositions for administration, singly or in combination, to a subject for the treatment or prevention of a disease or medical condition described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions or a pharmaceutically salt thereof such as acteate salt or trifluoroacetate salt, can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed my iontophoresis.

A therapeutic peptide or a pharmaceutically salt thereof such as aceteate salt or trifluoroacetate salt, can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. As one skilled in the art would appreciate, there are a variety of methods to prepare liposomes. (See Lichtenberg et al., Methods Biochem. Anal., 33:337-462 (1988); Anselem et al., Liposome Technology, CRC Press (1993)). Liposomal formulations can delay clearance and increase cellular uptake (See Reddy, Ann. Pharmacother., 34(7-8): 915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, Ann. Pharmacother., 34(7-8):915-923 (2000)). A polymer formulation for human growth hormone (hGH) has been used in clinical trials. (See Kozarich and Rich, Chemical Biology, 2:548-552 (1998))

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," Current Opinion in Biotechnology 6:698-708 (1995); Weiner, "Liposomes for Protein Delivery: Selecting Manufacture and Development Processes," Immunomethods, 4(3):201-9 (1994); and Gregoriadis, "Engineering Liposomes for Drug Delivery: Progress and Problems," Trends Biotechnol., 13(12):527-37 (1995). Mizguchi et al., Cancer Lett., 100:63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Dosage may also be determined empirically by detecting aromatic-cationic peptides in a biological sample from a subject. Biological samples obtained from a subject who has been administered aromatic-cationic peptides may be subjected to HPLC and/or MS to detect and characterize the aromatic-cationic peptides present in the subject's bodily fluids and tissues. Biological samples include any material derived from or contacted by living cells. Examples of biological samples include but are not limited to whole blood, fractionated blood, semen, saliva, tears, urine, fecal material, sweat, buccal, skin, cerebrospinal fluid, and hair. Biological samples also include biopsies of internal organs, organs removed for transplant or cancers. The presence of aromatic-cationic peptides in the biological sample is established by comparison to data obtained for reference samples such as those provided in Example 6. The levels of aromatic-cationic peptides present in the sample may serve as a basis to increase or decrease the dosage of an aromatic-cationic peptide or a precursor thereof, administered to a given subject, wherein the precursor may be an aromatic-cationic which is also a therapeutic agent or drug.

Typically, an effective amount of the aromatic-cationic peptides, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.1-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, and preferably until the subject shows partial or complete amelioration of symptoms of disease. Thereafter, the patient can be administered a prophylactic regime.

In some embodiments, a therapeutically effective amount of an aromatic-cationic peptide may be defined as a concentration of peptide at the target tissue of 10-11 to 10-6 molar, e.g., approximately 10-7 molar. This concentration may be delivered by systemic doses of 0.01 to 100 mg/kg or equivalent dose by body surface area. The schedule of doses would be optimized to maintain the therapeutic concentration at the target tissue, most preferably by single daily or weekly administration, but also including continuous administration (e.g., parenteral infusion or transdermal application).

In some embodiments, the dosage of the aromatic-cationic peptide is provided at a "low," "mid," or "high" dose level. In one embodiment, the low dose is provided from about 0.01 to about 0.5 mg/kg/h, suitably from about 0.01 to about 0.1 mg/kg/h. In one embodiment, the mid-dose is provided from about 0.1 to about 1.0 mg/kg/h, suitably from about 0.1 to about 0.5 mg/kg/h. In one embodiment, the high dose is provided from about 0.5 to about 10 mg/kg/h, suitably from about 0.5 to about 2 mg/kg/h.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

In some embodiments, multiple doses, or varying amounts of an aromatic-cationic peptide are administered to a subject. In some embodiments, the multiple doses or varying amounts of the peptide are administered throughout the course of a procedure (e.g., a surgery) or are administered throughout the course of a disease or conditions. For example, in some embodiments, the peptide is administered intravenously, for example during a surgery, and the amount of peptide provided to the subject is adjusted during the procedure. In other embodiments, the subject is administered a dose of peptide (e.g., orally or by injection, e.g., intradermal, subcutaneous, intramuscular, intravenous, intraosseous, and intraperitoneal) about once every 10 minutes, 15 minutes, 30 minutes, hour, 2 hours, 4 hours, 6 hours, 8 hours, 10 hours, 12 hours, once per day, once every other day, or once per week. In some embodiments, the amount of peptide present in the subject (the subject's peptide level) is monitored to determine the appropriate dose and schedule needed to maintain a desired peptide level in the subject. In some embodiments, peptide levels are determined periodically during administration, and/or are determined at one or more time points after administration. For example, in some embodiments, peptide levels are determined within a few minutes of administration, about 10 minutes, 15 minutes, 30 minutes, 1 hour, 2 hours, 4 hours, 6 hours, 8 hours, 10 hours, 12 hours, 24 hours, two days, 3 days 5 days, 7 days or 14 days after administration. In other embodiments, the subjects peptide levels are determined every 10 minutes, 15 minutes, 20 minutes, 30 minutes, hourly, every two hours, every 4 hours, every 6 hours or every 12 hours, for a predetermined time, such as during a surgical procedure. Depending on the determined peptide level, one or more additional doses may be provided to achieve a desired peptide level to maintain a therapeutic effect. In some embodiments, peptide levels may be found sufficient to delay an additional dose or doses.

In some embodiments, the detected levels of aromatic-cationic peptide are compared to aromatic-cationic peptide levels in a healthy control subject (e.g., a subject who has been administered substantially the same dose of the peptide via substantially the same route of administration). Additionally or alternatively, in some embodiments, the level of the peptide is determined in different organs, systems and/or fluids of a subject. In some embodiments, the level of the peptide is determined in different organs, systems and/or fluids of a subject and compared to peptide levels in comparable systems, organs, and fluids of a control subject. In some embodiments, such an analysis provides information regarding the availability of the peptide, and the transport of the peptide throughout the body of the subject as compared to the control. For example, the route of administration may be changed for a particular subject to optimize peptide delivery to a particular tissue or organ (e.g., to achieve a more localized distribution of the peptide). Additionally or alternatively, the route of administration could be changed for a particular subject to for a more systemic peptide distribution.

Method for identifying and determining the presence or amount (level) of an aromatic-cationic peptide in a subject sample are known in the art and include, but are not limited to HPLC and mass spectrometry.

As noted previously, in some embodiments, peptide levels are determined in a biological sample from the subject, and include, without limitation, blood samples, tissues samples, (e.g., organ or tumor biopsy samples), urine and saliva.

Also disclosed herein are kits for the detection of aromatic-cationic peptides. In some embodiments, the kits include a sample collection device to collect a sample from the subject, and a sample storage device for preservation of the biological sample. Depending on the intended method of detection, the sample is stored in an appropriate buffer or preservative, also provided in the kit. In some embodiments, a sample collector includes a container for liquid, such as a vial or tube (e.g., for blood, blood products, urine). In other embodiments, the sample collector is an absorbent material, such as a sterile cotton swab (e.g., to collect a buccal sample, saliva, nasal swabs, etc), a slide, a sterile paper, a card, a syringe, etc. The sample storage device may be any device that will encase and protect the sample during transport, shipment and/or storage. For example, in some embodiments, the sample storage device is a sealable tube.

In some embodiments, the kits also include instructions for obtaining a sample and properly storing the sample until analysis. In some embodiments, the sample includes a bodily fluid, one or more cells, a tissue or portion of an organ, a biopsy sample, and/and a portion of a tumor.

The mammal treated in accordance with the present methods can be any mammal, including, for example, farm animals, such as sheep, pigs, cows, and horses; pet animals, such as dogs and cats; laboratory animals, such as rats, mice and rabbits. In a suitable embodiment, the mammal is a human.

EXAMPLES

The present invention is further illustrated by the following examples, which should not be construed as limiting in any way.

Example 1—Aromatic-Cationic Peptides of the Present Technology Inhibit Inhibits $H_2O_2$ Generation by Isolated Mitochondria In this Example, the effects of the aromatic-cationic peptides of the invention on $H_2O_2$ generation by isolated mitochondria are investigated. $H_2O_2$ is measured using luminol chemiluminescence as described in Y. Li, H. Zhu, M. A. Trush, *Biochim. Biophys. Acta* 1428, 1-12 (1999)). Briefly, 0.1 mg mitochondrial protein is added to 0.5 ml potassium phosphate buffer (100 mM, pH 8.0) in the absence or presence of an aromatic-cationic peptide. Luminol (25 mM) and 0.7 IU horseradish peroxidase are added, and chemilumunescence is monitored with a Chronolog Model 560 aggregometer (Havertown, Pa.) for 20 min at 37° C. The amount of $H_2O_2$ produced is quantified as the area under the curve (AUC) over 20 min, and all data are normaliized to AUC produced by mitochondria alone.

It is predicted that the aromatic-cationic peptide will reduce the spontaneous production of $H_2O_2$ by isolated mitochondria. As such, the aromatic-cationic peptides are useful for reducing oxidative damage and are useful in the treatment or prevention of diseases or conditions that relate to oxidative damage.

Example 2—Aromatic-Cationic Peptides of the Present Technology Reduce Intracellular ROS and Increase Cell Survival To show that the claimed peptides are effective antioxidants when applied to whole cells, neuronal N2A cells are plated in 96-well plates at a density of 1×10+/well and allowed to grow for 2 days before treatment with tBHP (0.5 or 1 mM) for 40 min. Cells are washed twice and replaced with medium alone or medium containing varying concentrations of aromatic-cationic peptides ($10^{-12}$ M to $10^{-9}$ M) for 4 h. Intracellular ROS is measured by carboxy-$H_2$DCFDA (Molecular Probes, Portland, Oreg.). Cell death is assessed by a cell proliferation assay (MTS assay, Promega, Madison, Wis.).

Incubation with tBHP will result in an increase in intracellular ROS and decrease in cell viability. However, it is predicted that incubation of these cells with an aromatic-cationic peptide will reduce intracellular ROS and increase cell survival. As such, the aromatic-cationic peptides are useful for reducing oxidative damage and are useful in the treatment or prevention of diseases or conditions that relate to oxidative damage.

Example 3—Aromatic-cationic Peptides of the Present Technology Protect Against MPT Induced by Ca2+ and 3-Nitropropionic Acid To isolate mitochondria from mouse liver, mice are sacrificed by decapitation. The liver is removed and rapidly placed into chilled liver homogenization medium. The liver is finely minced using scissors and then homogenized by hand using a glass homogenizer. The homogenate is centrifuged for 10 min at 1000 g at 4° C. The supernatant is aspirated and transferred to polycarbonate tubes and centrifuged again for 10 min at 3000 g, 4° C. The resulting supernatant is removed, and the fatty lipids on the side-wall of the tube are carefully wiped off. The pellet is resuspended in liver homogenate medium and the homogenization repeated twice. The final purified mitochondrial pellet is resuspended in medium. Protein concentration in the mitochondrial preparation is determined by the Bradford procedure.

To investigate the localization of the aromatic-cationic peptides of the invention, approximately 1.5 mg mitochondria in 400 µl buffer is incubated with labeled aromatic-cationic peptide for 5-30 min at 37° C. The mitochondria are then centrifuged down and the amount of label is measured in the mitochondrial fraction and buffer fraction. Assuming a mitochondrial matrix volume of 0.7 µl/mg protein (Lim et al., J Physiol 545:961-974, 2002), the concentration of peptide in mitochondria can be determined. It is predicted that the claimed aromatic-cationic peptides will be more concentrated in mitochondria compared to the buffer fraction.

To investigate the effects of the aromatic-cationic peptides of the invention on mitochondrial membrane potential, isolated mouse liver mitochondria are incubated with 100-200 µM aromatic-cationic peptide. Mitochondrial membrane potential is measured using tetramethyl rhodamine methyl ester (TMRM). Addition of mitochondria results in immediate quenching of the TMRM signal which is readily reversed by the addition of FCCP, indicating mitochondrial depolarization. The addition of $Ca^{2+}$ (150 µM) results in immediate depolarization followed by progressive loss of quenching, indicative of MPT. Addition of aromatic-cationic peptide alone, even at 200 µM, is not predicted to cause mitochondrial depolarization or MPT. It is also predicted that the aromatic-cationic peptides will not alter mitochondrial function, including oxygen consumption during state 3 or state 4, or the respiratory ratio (state 3/state 4).

To show that the claimed peptides are effective at protecting against MPT induced by $Ca^{2+}$ overload, isolated mitochondria are pre-treated with aromatic-cationic peptide (10 µM) for 2 min prior to addition of $Ca^{2+}$. It is predicted that the aromatic-cationic peptides of the invention will increase the tolerance of mitochondria to cumulative $Ca^{2+}$ challenges.

3-Nitropropionic acid (3NP) is an irreversible inhibitor of succinate dehydrogenase in complex II of the electron transport chain. Addition of 3NP (1 mM) to isolated mitochondria causes dissipation of mitochondrial potential and onset of MPT. Pretreatment of mitochondria with the aromatic-cationic peptides of the invention is predicted to delay the onset of MPT induced by 3NP.

To demonstrate that the aromatic-cationic peptides of the invention can penetrate cell membranes and protect against mitochondrial depolarization elicited by 3NP, Caco-2 cells are treated with 3NP (10 mM) in the absence or presence of the aromatic-cationic peptides for 4 h, and then incubated with TMRM and examined under LSCM. In control cells, the mitochondria are clearly visualized as fine streaks throughout the cytoplasm. In cells treated with 3NP, the TMRM fluorescence is much reduced, indicating generalized depolarization. In contrast, it is predicted that concurrent treatment with the aromatic-cationic peptides of the invention will protect against mitochondrial depolarization caused by 3NP.

As such, the aromatic-cationic peptides are useful for preventing MPT and are useful in the treatment or prevention of diseases or conditions that relate to MPT.

Example 4—Aromatic-cationic Peptides of the Present Technology Protect Against Mitochondrial Swelling and Cytochrome c Release MPT pore opening results in mitochondrial swelling. This Example examines the effects of the aromatic-cationic peptides of the invention on mitochondrial swelling by measuring reduction in absorbance at 540 nm (A540). Once the absorbance is measured, the mitochondrial suspension is then centrifuged and cytochrome c in the mitochondrial pellet and supernatant is determined by a commercially-available ELISA kit. It is predicted that pretreatment of isolated mitochondria with the aromatic-cationic peptides of the invention will inhibit swelling and cytochrome c release induced by $Ca^{2+}$ overload. Besides preventing MPT induced by $Ca^{2+}$ overload, it is predicted that the aromatic-cationic peptides of the invention will also prevent mitochondrial swelling induced by MPP (1-methyl-4-phenylpyridiumion), an inhibitor of complex I of the mitochondrial electron transport chain.

As such, the aromatic-cationic peptides are useful for preventing MPT and are useful in the treatment or prevention of diseases or conditions that relate to MPT.

Example 5—the Peptides of the Present Technology Increase the Rate ATP Synthesis in Isolated Mitochondria This example will demonstrate the impact of peptides of the present technology on the rate of mitochondrial ATP synthesis.

The rate of mitochondrial ATP synthesis will be determined by measuring ATP in respiration buffer collected from isolated mitochondria 1 min after addition of 400 mM ADP. ATP will be assayed by HPLC. All experiments will be carried out in triplicate, with n=3. It is predicted that addition of peptides of the present technology to isolated mitochondria will increase the rate of ATP synthesis in a dose-dependent manner.

This result will demonstrate the peptides of the present technology are useful in methods and compositions for increasing the rate of mitochondrial ATP synthesis.

Example 6—Characterization of Aromatic-Cationic Peptides

Aromatic-cationic peptides of the present technology can be synthesized using solid phase synthesis and characterized using HPLC and MS. Exemplary HPLC and MS methods are provided in Examples 7 and 8 below.

Example 7—Detection of Aromatic-Cationic Peptides in a Biological Sample

This example demonstrates the detection of aromatic-cationic peptides in a biological sample by HPLC. Biological samples are collected from subjects in a suitable manner depending on the nature of the sample. Biological samples include any material derived from or contacted by living cells. Examples of biological samples include but are not limited to whole blood, fractionated blood, semen, saliva, tears, urine, fecal material, sweat, buccal, skin, cerebrospinal fluid, and hair. Biological samples also include biopsies of internal organs or cancers. Once obtained, the biological samples are stored in a manner compatible with the methods of detection until the methods are performed to ensure the preservation of aromatic-cationic peptides present in the sample.

Samples are loaded onto a 250×4.6 (i.d.) mm C18 5 μm column and subjected to a gradient of 0.1% trifluoroacetic acid in acetonitrile (Solution A) and 0.1% trifluoroacetic acid in HPLC-grade water (Solution B) according to the following scheme:

TABLE 6

| HLPC Methods | | |
|---|---|---|
| | A | B |
| 0.01 min | 7% | 93% |
| 25 min | 32% | 68% |
| 25.1 min | 100% | 0% |
| Flow rate | 1.0 ml/min | |
| Wave Length | 220 nm | |
| Load Volume | 10 μl | |

The presence of aromatic-cationic peptides in the biological sample is established by comparison to data obtained for reference samples such as those provided in Example 6.

The foregoing method is illustrative only, and should not be construed as limiting in any way. One of skill in the art will understand that the aromatic-cationic peptides described herein may be analyzed by a number of HPLC methods, such as those describe in Aguilar, *HPLC of Peptides and Proteins: Methods and Protocols*, Humana Press, New Jersey (2004).

Example 8 Detection of Aromatic-Cationic Peptides in a Biological Sample by MS

This example demonstrates the detection of aromatic-cationic peptides in a biological sample by MS. Biological samples are collected from subjects in a suitable manner depending on the nature of the sample. Biological samples include any material derived from or contacted by living cells. Examples of biological samples include but are not limited to whole blood, fractionated blood, semen, saliva, tears, urine, fecal material, sweat, buccal, skin, cerebrospinal fluid, and hair. Biological samples also include biopsies of internal organs or cancers. Once obtained, the biological samples are stored in a manner compatible with the methods of detection until the methods are performed to ensure the preservation of aromatic-cationic peptides present in the sample.

Samples are loaded in a 20 μl volume and analyzed under the following exemplary conditions.

TABLE 7

| MS Methods | |
|---|---|
| Probe | ESI |
| Nebulizer Gas Flow | 1.5 L/min |
| Curved Desolvation Line (CDL) | −20.0 v |
| CDL Temp | 250° C. |
| Block Temp | 200° C. |
| Probe Bias | +4.5 kv |
| Detector | 1.5 kv |

TABLE 7-continued

MS Methods

| T. Flow | 0.2 ml/min |
|---|---|
| Buffer | 50% H₂O-50% Acetonitrile |

One of skill in the art will understand, that the aromatic-cationic peptides described herein may be analyzed by a number of MS methods, such as those describe in Sparkman, *Mass Spectrometry Desk Reference*, Pittsburgh: Global View Pub (2000).

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all FIGS. and tables, to the extent they are not inconsistent with the explicit teachings of this specification.

Other embodiments are set forth within the following claims.

What is claimed is:

1. An aromatic-cationic peptide consisting of the amino acid sequence D-Arg-4-methoxy-2,6-dimethyltyrosine-Lys-Phe-NH$_2$, or a pharmaceutically acceptable salt thereof.

2. A pharmaceutical composition comprising the aromatic-cationic peptide or pharmaceutically acceptable salt thereof of claim 1.

3. The pharmaceutical composition of claim 2 further comprising a pharmaceutically acceptable carrier.

4. A method of reducing the number of mitochondria undergoing mitochondrial permeability transition (MPT), or preventing mitochondrial permeability transitioning in a mammal in need thereof, the method comprising administering to the mammal an effective amount of the aromatic-cationic peptide or pharmaceutically acceptable salt thereof of claim 1.

5. A method for reducing oxidative damage in a mammal in need thereof, the method comprising administering to the mammal an effective amount of the aromatic-cationic peptide or pharmaceutically acceptable salt thereof of claim 1.

6. A method for increasing the ATP synthesis rate in a mammal in need thereof, the method comprising administering to the mammal an effective amount of the aromatic-cationic peptide or pharmaceutically acceptable salt thereof of claim 1.

* * * * *